United States Patent [19]
Dublin, Jr. et al.

[11] Patent Number: 5,810,005
[45] Date of Patent: Sep. 22, 1998

[54] APPARATUS AND METHOD FOR MONITORING INTRAOCULAR AND BLOOD PRESSURE BY NON-CONTACT CONTOUR MEASUREMENT

[76] Inventors: Wilbur L. Dublin, Jr.; Lois G. Dublin, both of 6004 Tonkowa Trl., Georgetown, Tex. 78628; Richard E. Nieman; Randall E. Nieman, both of 7202 Montana Norte, Austin, Tex. 78731-2126

[21] Appl. No.: 102,968

[22] Filed: Aug. 4, 1993

[51] Int. Cl.$^6$ .................................................... A61B 3/16
[52] U.S. Cl. ............................................ 128/645; 128/748
[58] Field of Search ............................ 128/645–52, 664, 128/667, 672, 673, 685, 748, 666

[56] References Cited

U.S. PATENT DOCUMENTS

| | | | |
|---|---|---|---|
| 1,291,050 | 1/1919 | McLean . | |
| 1,331,777 | 2/1920 | Many . | |
| 1,419,134 | 6/1922 | Goldstein . | |
| 1,423,293 | 7/1922 | Amsler . | |
| 1,637,421 | 8/1927 | Lipschutz . | |
| 1,661,718 | 3/1928 | Davis . | |
| 1,743,461 | 1/1930 | Force . | |
| 2,314,514 | 3/1943 | Parsons | 73/51 |
| 2,366,645 | 1/1945 | Ollendorff | 73/80 |
| 2,519,681 | 8/1950 | Mages | 73/80 |
| 2,520,223 | 8/1950 | Sovatkin | 73/80 |
| 2,622,439 | 12/1952 | Copper | 73/80 |
| 2,656,715 | 10/1953 | Tolman | 73/80 |
| 2,708,847 | 5/1955 | Esterman | 73/80 |
| 2,708,928 | 5/1955 | Zenatti | 128/2.05 |
| 2,780,221 | 2/1957 | Posner | 128/2 |
| 2,831,478 | 4/1958 | Uddenberg et al. | 128/2 |
| 2,882,891 | 4/1959 | Husted | 128/2 |
| 2,968,941 | 1/1961 | Papritz | 73/80 |
| 2,984,099 | 5/1961 | Tolman | 73/80 |
| 3,049,001 | 8/1962 | Mackay et al. | 73/80 |
| 3,062,042 | 11/1962 | Gulden | 73/80 |

(List continued on next page.)

FOREIGN PATENT DOCUMENTS 1560192  4/1990  U.S.S.R. ................................. 128/645

OTHER PUBLICATIONS

Burris, et al., "Flattening of central corneal curvature with Intrastromal Corneal Rings of increasing thickness: An eye–bank eye study"; J Cataract Refract Sugg; vol. 19, Supplement 1993 (pp. 182–186).

Council on Scientific Affairs; "The Use of Pulse Oximetry During Conscious Sedation"; vol. 270, No. 12; Sep. 22/29, 1993.

Acton Research Corporation, CCD Imaging Spectrographs, Promotional Sheet, Circle No. 85.

EG&G Princeton Applied Research, CCD Technology, Promotional Sheet.

Frank Purcell, "Imaging Spectrographs Perform Multidimensional Spectroscopy", Technology Guide:Spectrometers, Laser Focus World, May, 1993.

Ophthalmology Times, "Corneal Mapping May Become Standard for Measuring Corneas".

Future Focus of Ophthalmology Value System (RBR) practice, Aug. 1, 1992.

Joann R. Schultz, Phoenix Laser Systems, Inc.

(List continued on next page.)

*Primary Examiner*—John P. Lacyk
*Attorney, Agent, or Firm*—Arnold, White & Durkee

[57] ABSTRACT

An apparatus and method is provided for monitoring internal pressure of a physiological vessel using non-contact contour measurement techniques. A pressure measuring system includes a light or acoustic source for impinging a beam on the vessel surface and a detector for detecting a reflected beam from the vessel surface, the system being mounted proximate to the vessel (e.g., an eye). The apparatus compares changes in vessel surface contour measurements with stored data relating changes in vessel surface contour with calibrated measurements corresponding to internal pressure of the vessel.

15 Claims, 15 Drawing Sheets

U.S. PATENT DOCUMENTS

| | | | |
|---|---|---|---|
| 3,070,087 | 12/1962 | Sittel | 128/2 |
| 3,070,997 | 1/1963 | Papritz et al. | 73/80 |
| 3,095,731 | 7/1963 | Schillinger | 73/80 |
| 3,136,152 | 6/1964 | Allen | 73/80 |
| 3,150,520 | 9/1964 | Mackay et al. | 73/80 |
| 3,181,351 | 5/1965 | Stauffer | 73/80 |
| 3,184,960 | 5/1965 | Murr et al. | 73/80 |
| 3,192,765 | 7/1965 | Keiper | 73/80 |
| 3,232,099 | 2/1966 | Motchenbacher | 73/80 |
| 3,246,507 | 4/1966 | Hyde | 73/80 |
| 3,248,934 | 5/1966 | Matalene | 73/80 |
| 3,266,301 | 8/1966 | Sovatkin | 73/80 |
| 3,272,001 | 9/1966 | Adise | 73/80 |
| 3,282,090 | 11/1966 | Posner et al. | 73/80 |
| 3,287,957 | 11/1966 | Martens | 73/1 |
| 3,290,927 | 12/1966 | Gambs | 73/80 |
| 3,299,882 | 1/1967 | Masino | 128/2.05 |
| 3,301,131 | 1/1967 | Benford | 350/149 |
| 3,304,769 | 2/1967 | Stauffer | 73/80 |
| 3,308,653 | 3/1967 | Roth | 73/80 |
| 3,330,152 | 7/1967 | Mackay | 73/80 |
| 3,338,089 | 8/1967 | Coombs et al. | 73/80 |
| 3,338,090 | 8/1967 | Coombs et al. | 73/80 |
| 3,359,789 | 12/1967 | Forse | 73/80 |
| 3,376,735 | 4/1968 | Garber et al. | 73/80 |
| 3,390,572 | 7/1968 | Murr | 73/80 |
| 3,406,565 | 10/1968 | Murr | 73/80 |
| 3,406,681 | 10/1968 | Zandman | 128/2 |
| 3,443,421 | 5/1969 | Posner et al. | 73/80 |
| 3,446,061 | 5/1969 | Draeger et al. | 73/80 |
| 3,449,945 | 6/1969 | Mohrman | 73/80 |
| 3,449,946 | 6/1969 | Gabriel et al. | 73/80 |
| 3,452,589 | 7/1969 | Hargens et al. | 73/80 |
| 3,470,432 | 9/1969 | Chubbuck | 318/127 |
| 3,470,736 | 10/1969 | Bartfay | 73/80 |
| 3,487,679 | 1/1970 | Yamamori | 73/80 |
| 3,511,085 | 5/1970 | Posner et al. | 73/80 |
| 3,531,984 | 10/1970 | Halberg | 73/80 |
| 3,538,754 | 11/1970 | Grolman et al. | 73/80 |
| 3,545,260 | 12/1970 | Lichtenstein et al. | 73/80 |
| 3,557,611 | 1/1971 | Adise | 73/80 |
| 3,564,907 | 2/1971 | Holcomb et al. | 73/80 |
| 3,572,100 | 3/1971 | Grolman et al. | 73/80 |
| 3,572,319 | 3/1971 | Bittner et al. | 128/2 |
| 3,585,849 | 6/1971 | Grolman | 73/80 |
| 3,597,964 | 8/1971 | Heine | 73/80 |
| 3,613,666 | 10/1971 | Hobbs | 128/2 |
| 3,628,526 | 12/1971 | Bigliano | 128/2.05 E |
| 3,651,689 | 3/1972 | Haddad | 73/80 |
| 3,677,074 | 7/1972 | Murr | 73/80 |
| 3,690,158 | 9/1972 | Lichtenstein et al. | 73/80 |
| 3,693,416 | 9/1972 | Dianetti | 73/80 |
| 3,703,095 | 11/1972 | Holcomb et al. | 73/80 |
| 3,714,819 | 2/1973 | Webb | 73/80 |
| 3,724,263 | 4/1973 | Rose et al. | 73/80 |
| 3,756,073 | 9/1973 | Lavallee et al. | 73/80 |
| 3,763,696 | 10/1973 | Krakau | 73/80 |
| 3,832,890 | 9/1974 | Grolman et al. | 73/80 |
| 3,832,891 | 9/1974 | Stuckey | 73/80 |
| 3,882,718 | 5/1975 | Kriebel | 73/80 |
| 3,913,390 | 10/1975 | Piazza | 73/80 |
| 3,934,462 | 1/1976 | Rende | 73/80 |
| 3,951,140 | 4/1976 | Eggleton et al. | 128/24 A |
| 3,952,585 | 4/1976 | Perkins et al. | 73/80 |
| 3,977,237 | 8/1976 | Tesi | 73/80 |
| 3,992,926 | 11/1976 | Berryhill | 73/80 |
| 4,064,743 | 12/1977 | Foddis | 73/80 |
| 4,089,329 | 5/1978 | Couvillon et al. | 128/2 T |
| 4,159,019 | 6/1979 | de Farias | 128/645 |
| 4,164,863 | 8/1979 | Ragsdale | 128/652 |
| 4,172,447 | 10/1979 | Bencze et al. | 128/648 |
| 4,192,317 | 3/1980 | Munnerlyn et al. | 128/646 |
| 4,209,021 | 6/1980 | Warming | 128/652 |
| 4,213,464 | 7/1980 | Katz et al. | 128/645 |
| 4,281,662 | 8/1981 | Brent | 128/676 |
| 4,305,399 | 12/1981 | Beale | 128/645 |
| 4,386,611 | 6/1983 | Kantorski et al. | 128/645 |
| 4,410,507 | 10/1983 | Chia et al. | 424/1.1 |
| 4,505,278 | 3/1985 | Alban | 128/774 |
| 4,523,597 | 6/1985 | Sawa et al. | 128/652 |
| 4,524,776 | 6/1985 | Withers et al. | 128/644 |
| 4,564,016 | 1/1986 | Maurice et al. | 128/645 |
| 4,580,559 | 4/1986 | L'Esperance | 128/303.1 |
| 4,621,644 | 11/1986 | Eilers | 128/652 |
| 4,624,235 | 11/1986 | Krabacher et al. | 128/652 |
| 4,628,938 | 12/1986 | Lee | 128/652 |
| 4,646,754 | 3/1987 | Seale | 128/774 |
| 4,665,923 | 5/1987 | Kobayashi | 128/648 |
| 4,705,045 | 11/1987 | Nishimura | 128/648 |
| 4,722,350 | 2/1988 | Armeniades et al. | 128/748 |
| 4,724,843 | 2/1988 | Fisher | 128/648 |
| 4,729,378 | 3/1988 | Trittenbass | 128/645 |
| 4,735,209 | 4/1988 | Foody | 128/652 |
| 4,747,296 | 5/1988 | Feldon et al. | 73/4 R |
| 4,759,370 | 7/1988 | Kozin et al. | 128/645 |
| 4,766,904 | 8/1988 | Kozin et al. | 128/652 |
| 4,770,181 | 9/1988 | Tomoda | 128/648 |
| 4,771,792 | 9/1988 | Seale | 128/774 |
| 4,799,489 | 1/1989 | Hideshima | 128/648 |
| 4,805,175 | 2/1989 | Knowles | 372/24 |
| 4,843,631 | 6/1989 | Steinpichler et al. | 382/43 |
| 4,888,490 | 12/1989 | Bass et al. | 250/561 |
| 4,935,635 | 6/1990 | O'Harra | 250/560 |
| 5,183,044 | 2/1993 | Nishio et al. | 128/645 |
| 5,269,310 | 12/1993 | Jones et al. | 128/667 |
| 5,313,941 | 5/1994 | Braig et al. | 128/667 |
| 5,333,610 | 8/1994 | Hirao | 128/664 |

OTHER PUBLICATIONS

Dr. Richard Nieman, "When Your Diagnoses Call For The Clearest, Most Accurate Measurement Of The Corneal Shape".

Hewlett Packard Optoelectronics Designer's Catalog 1985 High Resolution Optical Reflective Sensor (pp. 1–39 through 1–43); 1985.

Hewlett Packard Optoelectronics Designer's Catalog 1985 Optical Sensing for the HEDS–1000 (pp. 9–6 & 9–7).

VIEW 1
EYE LOOKING STRAIGHT AHEAD

VIEW 2
EYE ROTATED SO BEAM CONTACTS
CORNEA NEAR LIMBUS

VIEW 3
CONTINUED EYE ROTATION SO BEAM
CONTACTS CORNEA FURTHER FROM LIMBUS

ELECTRONIC RETINA
NORMAL VIEW

APPARATUS AND METHOD FOR MONITORING INTRAOCULAR AND BLOOD PRESSURE BY NON-CONTACT CONTOUR MEASUREMENT

BACKGROUND OF THE INVENTION

FIELD OF THE INVENTION

The present invention relates to methods and apparatus for non-contact measurement of internal pressure changes in physiological vessels or cavities.

BACKGROUND

Devices which measure blood pressure or the internal pressure of a physiological vessel or cavity are well known in the art. For example, devices used for measuring blood pressure in clinics or offices are generally known as sphygmomanometers, while those measuring fluid pressure within an eye are generally known as tonometers. The latter instruments measure the amount of tension on the eye's outer wall, allowing determination of fluid pressure within the eye. In order to measure outer wall tension, conventional tonometers often must have direct or indirect physical access to the outer wall to deform, displace or oscillate the outer wall. Analogously, measurement of blood pressure in most clinical situations requires application of an inflatable cuff to an arm or leg. In either case, special equipment is needed and, particularly in the case of tonometry measurements, the patient must visit a clinic or office for the measurement to be made.

Tonometry Principles

In general, most tonometers in use today work on either of two principles. The first principle involves applying a known pressure or force upon the wall and measuring the deformation produced. Instruments embodying this principle are known as impression or indentation tonometers. The second principle involves applying a known deformation upon the wall and measuring the force required to produce the deformation. Instruments using the second principle are called applanation tonometers. Under either principle, the wall must be physically manipulated, either by direct physical contact, such as with a probe or plunger, or by indirect contact, such as with an air puff or oscillating air stream.

Conventional tonometers are most often used for measuring intraocular pressure (IOP) by directly or indirectly flattening a pre-determined area of the cornea or the sclera. It is emphasized that though the normal usage is for the pressure discussed here to be referred to as intraocular pressure that it is actually the differential pressure between the inside of the eye and the ambient pressure outside. This differential pressure is consistent with results from conventional tonometry means. In order to contact these areas, the patient's eyes must be closely aligned with the tonometer so that accurate readings can be made. Such a procedure often involves a visit to a physician's office where a skilled operator performs the test. Furthermore, the operator may have to anesthetize the eye causing injuries to go undetected while the eye is under anesthetic.

Need for Repeat Measurements

Compounding these difficulties is the requirement for repeat measurements of both IOP and blood pressure (BP) to clinically follow the course and treatment of disease. The clinical value of any single measurement of IOP or BP may be reduced because long-term (e.g., weeks to months) pressure trends are always superimposed on shorter-term pressure variations. The latter variations can result, for example, from changes in body position, hydration or stress level. An additional confounding factor is the influence on IOP determinations of BP waveforms within the eye. The presence of these factors may make individual pressure determinations by current clinical methods relatively unreliable. Peak pressures, which may be important in assessing the severity of a disease process or the efficacy of treatment, may easily be missed because the measurement occurs before or after the peak. Accordingly, unless fairly continuous tests are performed over a relatively long period of time, measured BP and IOP may not detect pressure changes which would be clinically important for decisions related to the patient's health care.

SUMMARY OF THE INVENTION

The problems outlined above are in large part solved by the apparatus and methods of the present invention. While conventional tonometers (as well as sphygmomanometers) rely on invasive deformation of the vessel, the present invention provides long-term, repeatable measurement of pressure in a physiological vessel without physically manipulating or deforming the vessel by artificial means. In particular, the present invention determines internal pressure by non-invasive methods of measuring the contour or geometry of the vessel and relating changes in the contour to changes in pressure.

The present invention for non-contact determination of intraocular pressure and/or blood pressure trends is particularly convenient for home or ambulatory monitor of glaucoma or heart patients. The principle of the invention is to use the eye itself as the transducer with non-contact, non-intrusive means of detecting a "signature" proportional to pressure that may be "learned" by calibration at measured values against a precision tonometry standard. Data for IOP is afforded by signature analysis of contour changes at the limbus, related to IOP, by comparison to calibration data stored in the patient's data unit or the physician's office. Data for blood pressure comes from signatures of reflections from blood vessels on the sclera or from the carotid artery internal to the eye, in comparison to a calibration data set taken in the physician's office.

In preferred embodiments, an incident or measuring wave such as a light wave or acoustic wave (including electromagnetic waves of differing measuring wavelengths) is directed to the surface contour of a vessel. Alterations in the light wave reflected from the surface indicate changes in the surface contour, which in turn result from changes in internal pressure of the vessel relative to ambient. Thus, the present invention can be utilized to measure internal pressure within any physiological vessel having an expandable or elastic wall, the geometry of which changes in response to changes in internal pressure.

According to one aspect of the present invention, changes in IOP (including changes in BP) may be determined by observing changes in the contour geometry of the eye's outer surfaces in the limbus region (near the junction between sclera and cornea). Such determinations are possible because as IOP fluctuates, a dense ring of fibers within the limbus region (known as the annulus) tend to maintain the outer perimeter of the limbus. The annulus, while serving to anchor the ciliary muscles (and thus the lens), also acts to stabilize the limbus region and prevent the sclera and cornea from reacting to IOP changes as a single elastic membrane. Thus, while sclera and cornea expand and contract relatively independently in response to IOP changes, corresponding measurable changes occur in the angle between scleral and corneal surfaces. In preferred embodiments of the present invention, such angular changes are detected through their effect on the intensity and/or position of the beam or beams of light reflected from the eye when a light beam or beams are scanned across the scleral-corneal angle. Electrical signals proportional to changes in position of the reflected beam(s) may be provided, for example, by detectors comprising lateral-effect photodiodes or charge coupled devices. Such detectors are sensitive to position change in a reflected beam due to a change in angle of reflection from the eye; detector outputs may then subsequently be related to the corresponding changes in IOP which caused the change in angle of reflection. Photodiodes and charge coupled devices can provide electrical signals related to changes in reflected beam intensity and position, such signals as well as those from lateral-effect photodiodes being adapted for direct input to digital memory, for transmission to a remote digital computer, or for additional local processing.

Those skilled in the art will appreciate that in addition to changes in IOP, changes in the internal pressure of any vessel with elastic walls may be determined by techniques analogous to those described above. Changes in wall geometry need only be related to calibrated measurements of IOP and BP in the form of limbal contour signatures or pressure response contours respectively, values from which may then be used to estimate IOP and BP given only changes in wall geometry. For example, internal pressure changes in the carotid artery can be estimated by observing through the lens of the eye the blood-pressure induced configuration changes in the central retinal artery. Similarly, arterial blood pressure changes may also be estimated by simply observing, at a sufficiently rapid sampling rate, similar angle changes to the scleral-corneal angle used to estimate IOP changes. In the latter case, blood-pressure waveforms may be electronically separated from other pressure waveforms present within the eye (and detectible at the scleral-corneal angle) because of their relatively high frequency and distinctive wave shape. Blood pressure also may be observed at the vessels on the surface of the sclera.

Short-term changes in the scleral-corneal angle (resulting from corresponding changes in IOP) can be quickly and easily measured and interpreted with the apparatus and methods of the present invention, thus facilitating improved medical care. Signals generated by reflected waveforms striking the detector need only be compared with stored information in the form of signatures or contours. Values from the first type of stored information, called a limbus contour signature, allow conversion of alterations in reflected waveform electrical signals to changes in IOP. Such stored information comprises experimentally derived or predicted relationships between estimated IOP changes and alterations in reflected waveform electrical signals (e.g., changes in reflected beam intensity or position). For each IOP application of the present invention (i.e., for each patient), calibrated measurements of IOP changes may be stored and used to construct a unique limbus contour signature relating alterations in reflected waveform electrical signals to changes in IOP. Limbus contour signatures in most patients are stable over extended periods, thereby reducing the need for periodic recalibration.

Analogous procedures are used to relate alterations in reflected beam intensity or position to changes in BP as determined by sphygmomanometer. Note that alterations in reflected waveform electrical signals (due to intensity or position changes) may be accurately attributed to either IOP or BP using the unique characteristics of each pressure waveform (e.g., frequency content and periodicity) to allow separation and quantification. Obtaining numerical BP estimates by conversion of electrical signals attributed to BP changes is accomplished by reference to a second type of stored information called a pressure response contour. This response contour represents correlated values of BP change and alterations of electrical signals representing change in the BP component of IOP. Knowing the measure of alteration in the electrical signal (whether due to change in intensity or position) allows one to estimate a corresponding change in BP.

Repeatable IOP and BP measurements are easily obtained in practice by placing the apparatus of the present invention on a fixed plane or axis proximate to the eye; eyeglasses worn by the patient can provide convenient mounting points. Limbus contour signatures and pressure response contours may be stored in a remote memory medium (i.e., in the physician's office) to provide comparison with alterations in reflected waveform signals and thus to aid in the diagnosis and treatment of eye disease. Pressure response contours may also be stored in a device carried by a patient, so that reflected waveform signals may be quickly converted to pressure measurements and the patient warned of any dangerous rise or trend in IOP or BP. In this application, for example, IOP rises not caused by normal physiological activity (i.e., heart beat or body position changes) or the external environment (atmospheric pressure or temperature changes) can be detected by statistical moving averages of angle measurements accumulated in the memory medium and interpreted by reference to the limbus contour signature. Accordingly, the present invention is capable of recording changes in IOP or BP relative to a baseline; trends in IOP and BP can be detected and warning given the patient (e.g., by audio alarm or vibrator) that immediate medical treatment should be administered to prevent injury (e.g., cardiac damage or certain complications of glaucoma).

Broadly speaking, the pressure measuring apparatus of the present invention comprises a light emitter placed proximate to a physiological vessel for emitting a light beam which impinges upon a portion of the outer surface of the vessel which may be anisotropic. A light detector is spaced relative to the emitter for detecting alterations in a reflected beam resulting from angular configuration changes in the outer vessel surface, the light beam being reflected from a plurality of points on the outer surface. The detector produces electrical signals related to alterations in the reflected beam, and a signal processor may then be coupled to the light detector for comparing reflected beam electrical signal alterations with values from a limbus contour signature or pressure response contour calibrated as a function of measured pressure within the vessel.

The light emitter includes either a light emitting diode or a laser. Alternatively, acoustical or other forms of waves capable of reflection can be emitted rather than light. In either case, an appropriate transducer converts relative alterations in the reflected wave into electrical signals which represent angular changes in the surface; the signals may then be processed by the signal processor. Thus, in preferred embodiments of the present invention, the scleral-corneal region itself becomes a transducer for IOP and BP changes.

According to another aspect of the present invention, the light emitter and detector are coupled (as a transceiver) to a scanner which moves the emitter and detector in close proximity across the outer surface of the eye. The scanner includes a platform having the emitter and detector fixed in spaced relation to one another, and a motive source or drive attached to the platform for moving it in close proximity across the eye surface. Alternatively, the scanner may be stationary and the surface of the eye may move in relation to the scanner to provide the requisite scanning function. Such motion may be induced by normal eye or head motion relative to an eyeglass frame on which the transceiver is mounted.

According to another aspect of the invention, the detector comprises at least one photodetector configured to receive the reflected light beam and convert the beam to an electrical signal. At least one amplifier of common circuit design is coupled to a photodetector for amplifying the electrical signal. A local memory medium can be electrically coupled to the output of the amplifier for accumulating the electrical signals, wherein the electrical signals correspond to changes in surface angularity represented by the light beam reflected from the outer surface of the vessel. Once accumulated in the local memory, the electrical signals can be processed locally within the system to separate and identify signals relating to changes in BP from those relating to IOP and downloaded for comparison locally or remotely with accumulated sets of stored electrical signals (limbus contour signatures and pressure response contours). In some embodiments, a remote computer is used for performing the necessary computations and for estimating IOP and BP as functions of, or relative to, alterations in a waveform reflected from the eye surface or from internal to the eye through the pupil lens. Those skilled in the art will recognize that estimates of IOP and BP can also be made locally with a computer or processor carried by the patient.

According to another embodiment of the present invention, an IOP/BP measuring apparatus is provided comprising a light emitter to be placed proximate an outer surface of an eye and at least one photodetector spaced relative to the emitter. The light emitter preferably produces one or more light beams scanned across the outer surface at a limbus region between or adjoining the sclera and cornea of the eye. The photodetector converts the intensity or position of light beams reflected from the limbus region to corresponding electrical signals which are convertible by use of values from the limbus contour signature and pressure response contours from the central retinal extension of the carotid artery to IOP and BP estimates. Prior to conversion, the signals may be encoded to digital form by an analog-to-digital converter coupled to the photodetector. A local memory medium may be provided for accumulating the digital data over a period of time commensurate with the rate of changes in contour of the limbus region. Photodetectors usable in the present invention comprise those sensitive to changes in intensity and/or position of an incident light beam, whether of visible or non-visible light. Suitable photodetectors include, but are not limited to photodiodes, lateral-effect photodiodes, and charge coupled devices.

According to another aspect of the present invention, the light emitter and photodetector are coupled to a localized portion of an eyeglass frame movable in close proximity to the limbus region. The light emitter and photodetector are fixed in space relation to each other and moveable in relation to the limbus region. Reliance may then be placed on the repeatable involuntary movement of the eye in its socket in association with a turn of the head. Such eye movement will result in a scanning of the light beam from the emitter over the limbal region. Alternatively, one may employ prismatic transmission or faceted reflective deflectors to, periodically or on command, deflect the light beam from the emitter to scan the limbus zone.

The present invention also contemplates a method for measuring IOP and BP which includes repeatedly scanning one or more light beams across a limbus region adjacent to and between the sclera and cornea of an eye, the surface of the sclera, or the central retinal artery. The light beam intensities and/or positions reflected from the limbus region, together with separately determined (calibrated) IOP and BP determine the shape of the limbus contour signature and pressure response contours and thus the conversion from intensity/position data to pressure data. Periodic recalibration of the signature and contour using independent pressure measurements gives assurance of accurate determinations of IOP; the spacing of such recalibrations depends on clinical estimates of the accuracy of each conversion and periodic rechecks of calibration during routine office visits.

BRIEF DESCRIPTION OF THE DRAWINGS

Other objects and advantages of the invention will become apparent upon reading the following detailed description and upon reference to the accompanying drawings in which.

Figure 1:
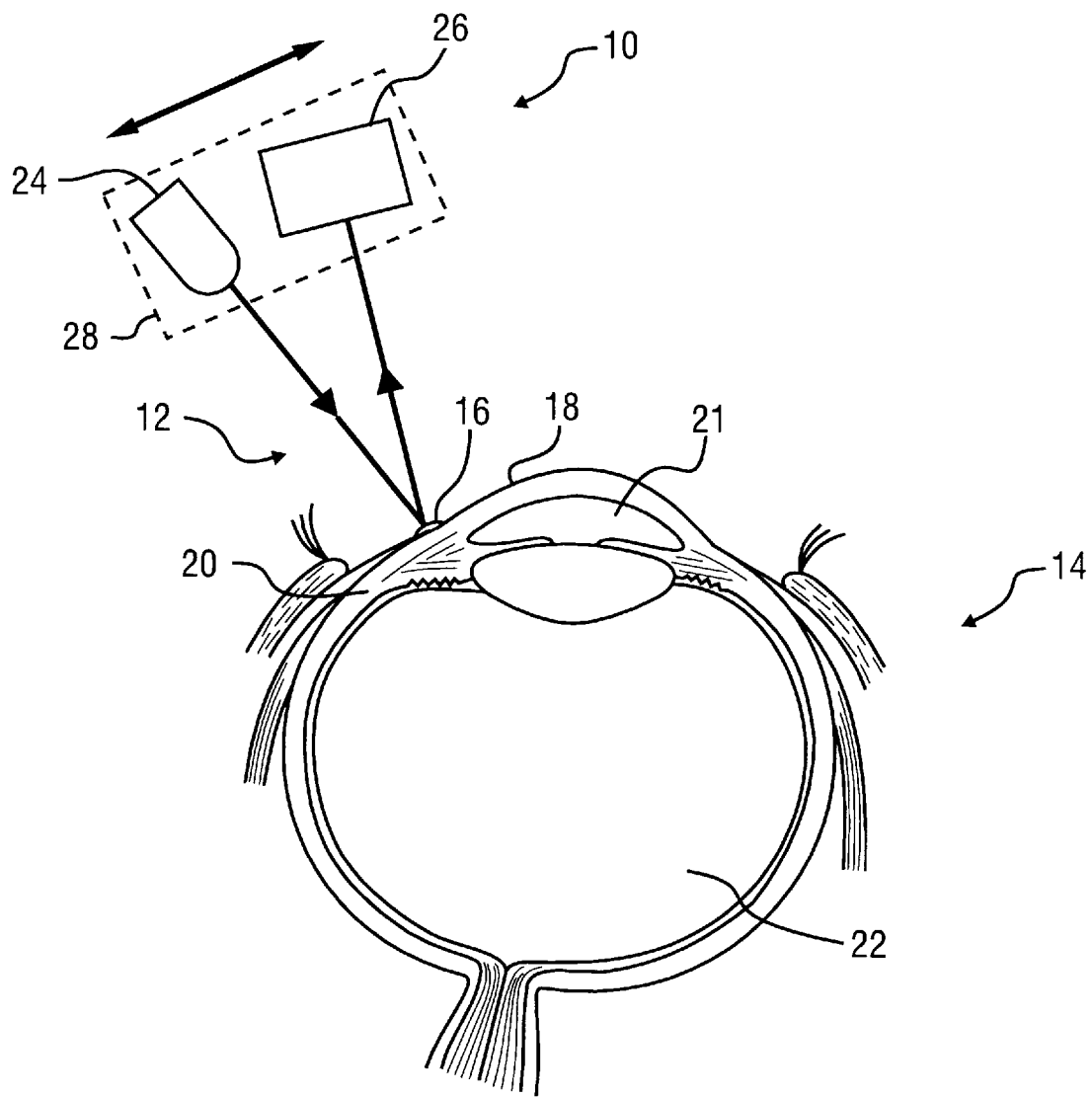
FIG. 1 is a cross-sectional view of an eye having a pressure measuring apparatus according to the present invention arranged in optical communication with a limbus region of the eye.

While the invention is susceptible to various modifications and alternative forms, a specific embodiment thereof has been shown by way of example in the drawings and will herein be described in detail. It should be understood, however, that the drawings are not intended to limit the invention to the particular form disclosed, but on the contrary, the intention is to cover all modifications, equivalents and alternatives falling within spirit and scope of the invention as defined by the appended claims.

DETAILED DESCRIPTION OF THE INVENTION

There are two main physical principles in this invention; first, the angle of incidence of beams relative to a reflecting surface equals the angle of reflection; and second, that the structure of the eye is, geometrically, the intersection of two membranes of substantially spherical shape, following the laws of mechanics. These laws of mechanics are comprised by a set of four conditions:

1. Stress-strain relationships (Hooke's Law)
2. Strain displacement relationships (Continuum of the eye)
3. Equilibrium conditions (fluid pressures/membrane stresses)
4. Boundary conditions (Ambient and physiological conditions)

The eye satisfies all of these conditions simply by its existence. It is comprised of fluid filled dual membranes (Cornea and Sclera), of near spherical shape, joined and reinforced at the limbus by a fibrous ring that acts to react the forces of the ciliary muscles in changing the shape of the elastic lens to focus the image on the retina. The external contour of the eye is the result of the shape, size, and elasticity of the membranes and the differential pressure (IOP) between the inside of the eye relative to that outside (ambient) the eye. Similarly, the carotid artery is a network of vessels of cylindrical form anchored to the retina by elastic tissue; vessels on the surface of the sclera are of similar form.

The present invention affords determination of IOP, from limbus contour signature; and/or blood pressure, from reflections off blood vessels inside the eye, or on the sclera, and during the patient's daily routine to a degree never before possible. Detection of a high pressure event allows medication to relieve the pressure before permanent damage occurs.

The aqueous humor in the anterior chamber directly behind the corneal membrane is a part of the eye's focusing apparatus and the source of IOP. Aqueous humor is generated in the ciliary body to augment the optical refraction of the lens; the change in thickness of aqueous in the anterior chamber acts with the shape change of the lens to focus the image on the retina. Aqueous is ported from the anterior chamber through the trabecular meshwork. IOP is transmitted to the vitreous humor by equilibrium of fluid pressure. The external contour of cornea and sclera at their junction, called the limbus, is determined by the difference between internal and ambient pressure (IOP); the stresses and strains within the corneal and scleral membranes; and the stresses and strains in the fibrous reinforcement at the limbus. Eye structures are as unique as fingerprints between individuals, and the external shape of an eye must follow the laws of mechanics, with the fluid pressure difference between the inside and outside of the eye in equilibrium with the stresses in the membranes and fibers. The geometric shape of an eye is a function of IOP that can be learned from signature analysis of indicators to that shape.

An eye is similar to a balloon, where size and shape depend on the difference in internal and external pressure. The difference in pressures is reacted by change in tensile stress that stretches or allows the membranes to contract like the rubber in a balloon. For an eye to maintain its shape, the internal pressure must be greater than the ambient pressure; otherwise, the membranes would not be taut and the shape of the eye would be incoherent like that of an empty balloon. Ambient pressures vary widely for an eye; examples varying from that of a fraction of an atmosphere for a climber atop Mount Everest, to that of an extra atmosphere for every 30 feet of depth for a scuba diver while diving. Though the absolute values of ambient pressure are different in these examples, the differential pressure, IOP, is similar except for secondary effects of the compressibility of the aqueous and vitreous humors (fluids) themselves. For practical purposes these fluids are incompressible.

As previously discussed, the aqueous humor in the anterior chamber is the source of IOP. Glaucoma is failure of the regulating system for IOP; usually associated with the inability to port the aqueous humor from the anterior chamber. The pressure generated by the aqueous humor is transmitted to the vitreous humor, inside the sclera, to equalize the pressure therein. The shape of the eye is the result of equilibrium between IOP, and the stresses in its physiological structure. The shape, then, is a unique function of IOP for each eye.

In summary, this invention is non-intrusive to the eye from anything other than a beam of coherent energy, such as light, that will obey the law of optical reflection from the eye's surface. The physical feature giving the greatest signal is the limbus, with maximum deflection occurring immediately on crossing the limbus' discontinuity. The response of the eye to IOP is governed by the laws of mechanics that are independent of the apparatus of the invention.

Measurement of Intraocular Pressure Changes

Referring now to FIG. 1, a pressure measuring apparatus 10 (partially shown) is brought in close proximity with a limbus region 12 of an eye 14. Apparatus 10 is used for measuring contour displacements which is related to pressure within any physiological vessel having an elastic or flexible outer membrane which changes contour in relation to changes in internal pressure. An eye 14 includes elastic membranes surrounding aqueous fluid 21 and vitreous fluid 22 which change internal pressure over a period of minutes, hours, days, months or years. Pressure readings within eye 14 are preferably taken with reference to regions which change shape or contour in conjunction with changes in IOP. Specifically, limbus region 12 includes a fibrous ring structure region near the annulus 16 bound between cornea 18 and sclera 20. Changes in IOP of the aqueous fluid 21 and vitreous fluid 22 cause fluctuations in the outer contour or shape of cornea 18 and sclera 20 respectively.

Figure 2:
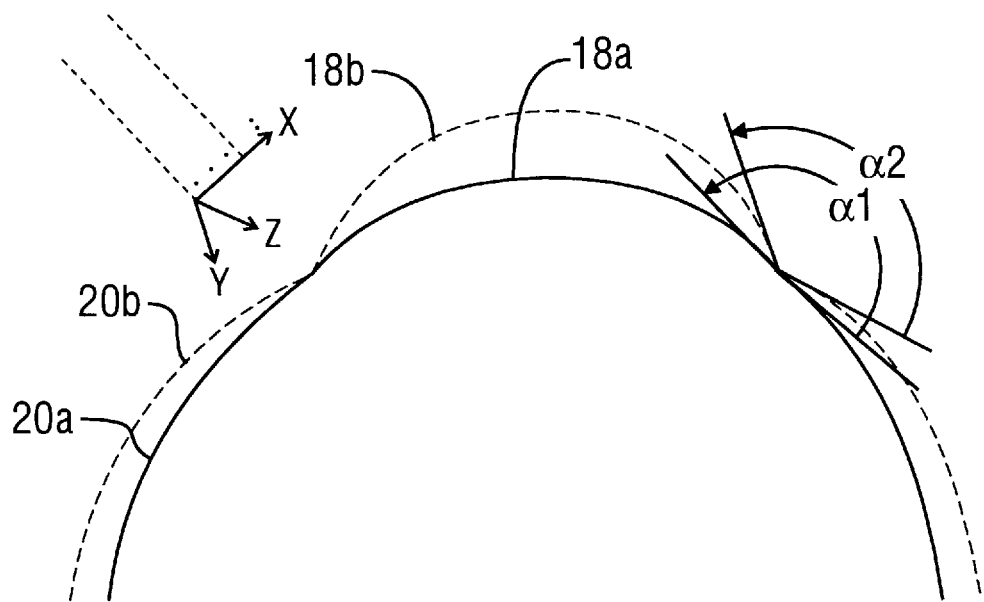
FIG. 2 is a cross-sectional view of the limbus region of the eye having cross-sectional contour geometries differing as a function of intraocular pressure within the eye.

Pressure measuring apparatus 10 includes a light emitter 24 and light detector 26 fixed in space relationship to each other on a platform 28. It is to be appreciated that although light is the preferred reflective medium, other waveforms can be used to project reflected information from limbus region 12. For example, sound waves or acoustical waves may be used to provide analogous results, i.e., to present waveform alterations indicating relative positional changes in the outer contour of the limbus region 12 with the proviso that the beam displacement relative to the eye be separately measured to construct the limbus contour. Platform 28 can be arranged to scan in close proximity to limbus region 12 in one direction or in both directions, as indicated in FIG. 1. Movement of platform 28 provides optical scanning of one or more emitted and reflected light beams across the entire limbus region. Alternatively, platform 28 can be stationary and normal sweep movement (i.e., rotation) of the eye may provide the necessary scanning of the waves across the limbus region 12. All that is necessary is that apparatus 10 and limbus region 12 move or scan in relation to each other, preferably along a single scanning axis, defined as the X-axis as shown in FIG. 2 and described below. The optical sensor provides a signal related to z axis displacement to the eye's surface to define the limbus contour. Note that a plurality of detectors 10 (not shown) may be arranged to provide a holographic interferogram three dimensional real image of the limbus region 12.

FIG. 2 illustrates the expansion or contraction of the outer walls in and around limbus region 12 as a function of pressure. For this example, the reinforcement at the limbus is idealized as being the dominant stiffness so that the annulus remains relatively inextensible, and the limbus angle becomes more acute with increasing pressure. In actuality, due to the fact that eyes are unique physiological structures, this may, or may not, be the case. If the reinforcement at the annulus is relatively soft in comparison to the corneal and scleral membranes, an increase in pressure will tend to take the eye's structure in the direction of becoming a sphere of uniform radius, or with the limbus' angle becoming less acute with increasing pressure. Specifically, rise in aqueous pressure causes cornea 18 to increase from its outer position 18a to 18b. Likewise, sclera 20 can expand from a low pressure position 20a to a high pressure position 20b. Because of the constraint by annulus 16, the point or points of measurement of angles $\alpha_1$ and $\alpha_2$ are relatively fixed on the eye, and it is one purpose of the present invention to measure angular changes $\alpha_1$ and $\alpha_2$ for the low pressure contour and high pressure contour positions, respectively. Several examples of devices and methods by which the contour shapes can be measured during scan along the X-axis are described below.

Figure 3:
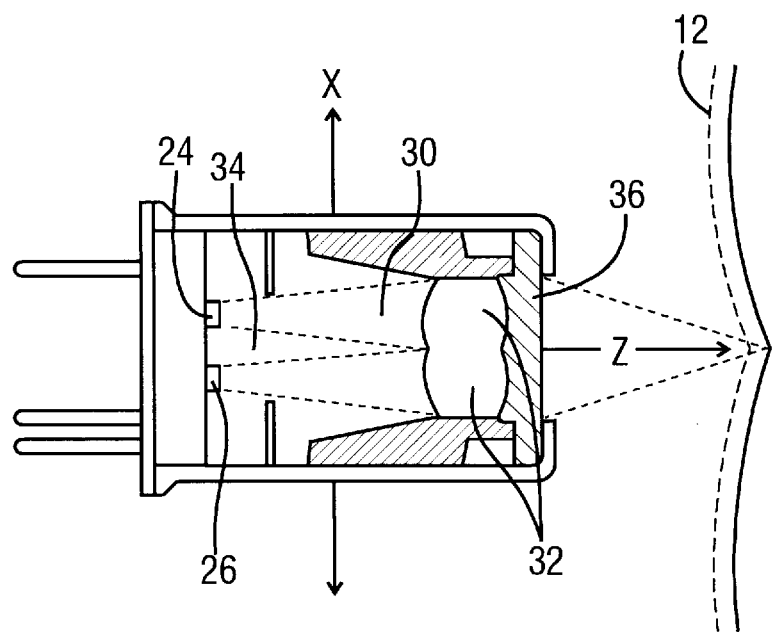
FIG. 3 is an embodiment of an optical reflective sensor according to the present invention arranged in close proximity with an eye's limbus region.

There are various devices which can optically measure three-dimensional contour of an object. One form of optical contour sensor using light emitting diodes and photodiodes may be purchased as Model No. HBCS-1100 from Hewlett Packard, Inc. It is important to note, however, that an optical contour sensor like the HBCS-1100 using light emitting diodes in conjunction with an aspheric lens as shown in FIG. 3 generally produces piece-wise linearity both before and after a set focal point distance. As will be described later, and illustrated in FIG. 4, linearity varies depending upon the distance to the object relative to the point Zmax. Accordingly, while light emitting diodes used in Model No. HBCS-1100 are one form by which the present invention may be practiced, varying other forms having desirable advantages may also fall within the scope and spirit of this invention.

Pressure measuring apparatus 10 illustrating Model No. HBCS-1100 optical sensor 29 is shown in FIG. 3. Sensor 29 includes a transmission path 30 formed between emitter 24 and detector 26. Sensing occurs by having an object, in this case limbus region 12, placed at a distance along the Z-axis to obstruct transmission path 30, or complete path 30 by reflecting the emitter beam to the detector. In either case, the transmissive or reflective sensing configuration allows non-intrusive optical readings be taken corresponding to the intensity and/or position of the reflected beams.

The characteristics of the transmission path can be estimated through the use of an optical transfer function, OTF. The OTF is the ratio of the total optical flux transmitted to the amount of flux and the angularity (or position) of the beam reflected back to detector 26. As will be described below and illustrated in FIG. 4, the amount of reflected optical flux or light received on detector 26 is optimum for this embodiment when the nominal transmission path is set at a specific distance.

As illustrated in FIG. 3, transmission path 30 represents a path of travel between emitter 24 and detector 26. The path length is dependent upon the spacing between sensor 29 and limbus region 12 along the Z-axis. Placed along path 30 is a pair of lenses 32, an aperture 34 and glass window 36. At least part of apparatus 10 can therefore be packaged and sold as a single sensor unit 29, Model No. HBCS-1100, of which a full description is provided in *Optoelectronics Designer's Catalog*, Hewlett Packard (1985), pp. 1–39 to 1–44, the disclosure of which is incorporated herein by reference.

Figure 4:
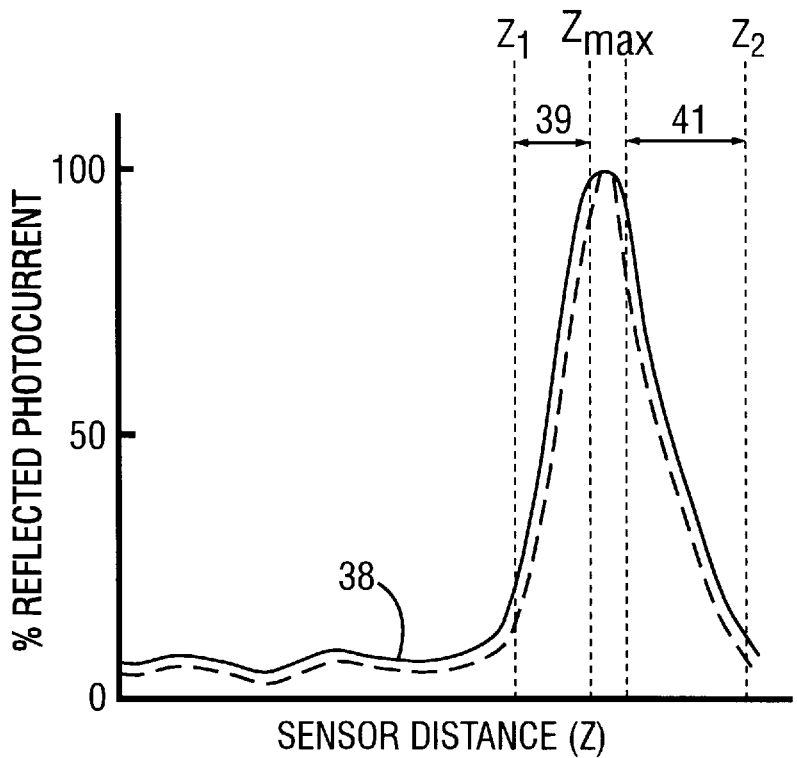
FIG. 4 represents the output of the HBCS-1100 sensor applied as in the present invention to sense distance between the sensor and the limbus region as a function of reflected photocurrent.

Apparatus 10, which includes an optical reflective sensor 29, determines the outer contour of region 12 by measuring the spacing between apparatus 10 and region 12 as a function of percent reflected photocurrent as illustrated in FIG. 4. Apparatus 10 can be designed such that an optimal spacing exists between sensor 29 and limbus 12 such that 100% reflected photocurrent impinges upon detector 26 at a particular spacing distance ($Z_{max}$). As apparatus 10 moves relative to region 12 along the X-axis, the percent reflected photocurrent will either increase or decrease depending upon whether the transmission path is advancing toward or away from, respectively, the optimal path length. $Z_{max}$ is preferably set at a relatively fixed Z-axis distance between sensor 29 and the annulus region 16. On either side of $Z_{max}$, percent reflected photocurrent decreases from the optimal 100% as shown in FIG. 4. Zones 39 and 41 are piecewise substantially linear segments that precede and follow the maximum photocurrent point at the focal point of the aspheric lens. This means that the sensor, in order to avoid duplicate outputs over its range of operation should be positioned to function solely in either zone 39 or zone 41 so that the output slope remains monotonic over the range of operation. Zone 41 has advantages over zone 39 for the present invention because its range is greater than that of zone 39 (both absolute and usable distance from the limbus is greater) and the sensor would have greater clearance with the eye or lashes. Zone 39 has an advantage over zone 41 in that it is of greater sensitivity and linearity, with a positive slope. The limbus contour signature (and pressure response contour) will allow accurate estimation of IOP and BP in spite of the non-linearity regardless of the zone chosen. The repeatability of the zone used, however, is important to this application. Lens characteristics may be modified to tailor the preferred zone for use.

The sensor reflector distance or transmission path length used in Hewlett Packard Model No. HBCS-1100 is fairly short and narrow. However, a longer or a broader range of detectable distances, Z, can be measured embodying the principles of Model No. HBCS-1100. For example, emitter 24 output can be amplified and different lenses 32 can be used to refocus the beam so that the sensor 29 can be placed from 2 millimeters to several centimeters away from the vessel or region 12. Other forms of photodetectors can also be used. The most popular types of photodetectors suitable for use with the present invention include: Charge coupled devices (CCD's), PIN photodiodes, lateral-effect photodiodes or avalanche photodiodes. Detector 26, using a highly sensitive avalanche photodiode of common design, provides internal gain to the resulting electrical signal thereby useable for detecting reflected waves when path lengths are relatively long. Photodiodes provide optical-to-electrical conversion resulting in an analog current which can be manipulated using conventional circuit techniques. In particular, electrical signals from the photodetectors can be converted from analog-to-digital (A/D) format using standard converters such as a successive approximation A/D converter or a high speed A/D flash converter.

Example 1

A general embodiment of the present invention is illustrated in the following example. This example uses the sweep of a beam over the limbus at either approximate right angle, or tangency, to the limbus to produce the limbus angle signatures required. In the initial case of sweep at near right angle to the limbus, the eye may be stationary while the beam sweeps relative to the eye. In the case where the beam sweeps tangent to the limbus, it is necessary to rotate the eye about a vertical axis so that the limbus crosses the plane of sweep. This is an embodiment that will accomplish the same effect as the subsequent multi-beam unit of EXAMPLE 4, through the kinematic inversion of sweeping a single beam through an essentially similar multiplicity of position, in lieu of a multiplicity of beams in fixed positions.

Laser Measurement of Eye Contour

Figure 5:
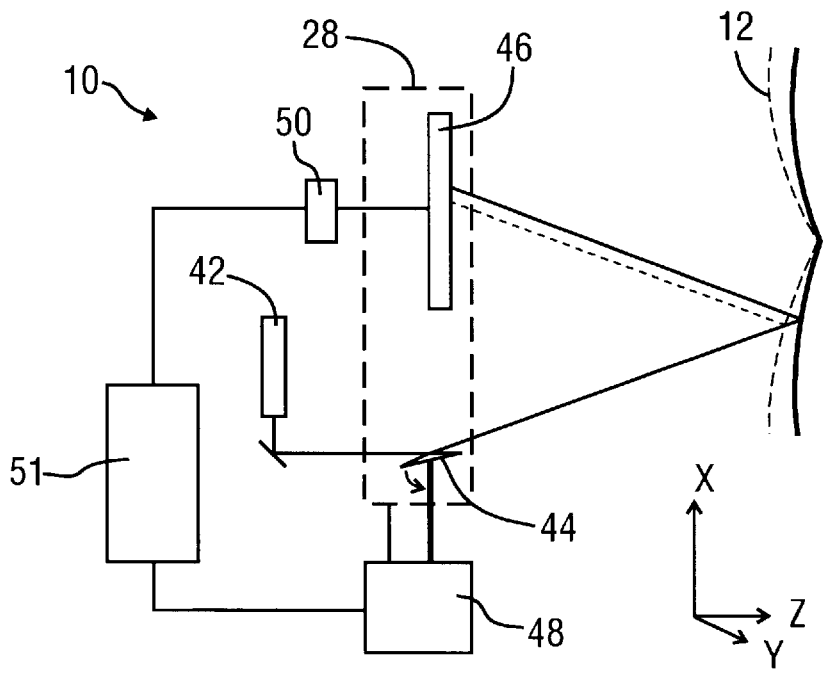
FIG. 5 is another embodiment of an optical reflective sensor according to the present invention arranged in close proximity with an eye's limbus region.

Utilization of a laser for three-dimensional contour measurement is illustrated in FIG. 5. In particular, a three-dimensional optical measuring technique can be employed as described in U.S. Pat. No. 4,935,635 (herein incorporated by reference). Three-dimensional contour measurement includes a laser diode 42, polygonal reflector 44 and photodiode array 46. Further included is a linear stepper motor 48 having two shafts, one shaft for providing rotation to reflector 44 and the other shaft for driving a threaded screw cam attached to moveable platform 28. The laser 42 and photodiode array 46 functions similar to sensor 29 of FIG. 3 in that relative spacing along the Z-axis between apparatus 10 and limbus region 12 are sensed to provide a two-dimensional contour reading. The position of the returning imaged beam spot along the length of photodiode array 46 indicates the contour or Z-axis distance between the particular point on region 12 and apparatus 10.

Each measurement of intraocular pressure is achieved by performing one scan of platform 28 across limbus region 12. Each scan produces a reflective beam positional change upon array 46 as the beam travels across limbus region 12. As the contour changes during each scan, the angle of incidence changes and the corresponding reflected wave position upon the array changes. It is the relative change in the position upon the array 46 that determines a proportional difference in depth sensed on the eye surface. This technique of depth detection to measure three-dimensional contour is commonly described in Patent No. '635 as "triangulation". The y-axis dimension is afforded by separate sweeps at incremental changes in y.

An encoder such as, for example, an analog-to-digital converter 50 counts each photodiode on a pixel-by-pixel basis as it is scanned from the photodiode array 46. The resulting counter value representation of digital data is latched and stored into a local memory medium 51, whereby it can be later read by a signal processor 52, illustrated in FIG. 6 and described below.

The choice of local or remote processing of reflected waveform signals may depend on availability of adequate computing power near where the measurements are generated. In this regard, neural or "neuron" network electronic chips which are now available may influence the choice. One such device contains three microprocessors, several channels of input/output (I/O) communications and significant on-board random-access and read-only memory.

Neural chips, in combination with proper on-board software, are thus capable of converting reflected waveform signals to estimated IOP and BP changes by application of values derived from the limbus contour signature and/or the pressure response contour. Processing of angle change (reflected waveform) data to yield estimated IOP and BP in conventional units of measurement through application of a pressure response profile is also possible on the chips. Thus, for example, either physician or patient may obtain an IOP or BP readout in mm-Hg in nearly real time. The various I/O options make it possible to provide appropriate warnings to the patient and even to calculate proper dosage of medication and administer it automatically. Simultaneously, such chips may process data for storage in an on-board memory or for direct transmission to a physician's office via radio telemetry or modem and land line. Such transmission would allow prompt interpretation of the data by skilled medical personnel; impending acute exacerbations of glaucoma or arterial hypertension may be monitored closely and treated promptly to avoid or reduce morbidity.

General operation and setpoints for the counter of analog-to-digital converter 50 and latches within medium 51 are determined based upon which pixel on the array is currently being interrogated. Other counters may also be available to determine X-axis position of platform 26 via stepper motor 48 and X-axis position of platform 26 in conjunction with polygonal reflector 44 position. Thus, latched digital data corresponding to electrical signals placed in memory 51 also provide indicia of the relative position of the X and Y scanning axes via connection to motor 48.

The light transmitted from laser 42 has a coherent signature which is sufficiently unique to distinguish it from ambient light. The angular contour signature of limbus region 12 is indicated every time the eye rotates about its vertical axis far enough for the limbus to pass through the beam. An inclination of the eye about an axis in the horizontal plane results in deflection of the beam in a plane normal to the normal scan plane. This data may be recorded to allow calculation of the eye position as well as the limbus signature for subsequent determination of intraocular pressure.

Figure 6:
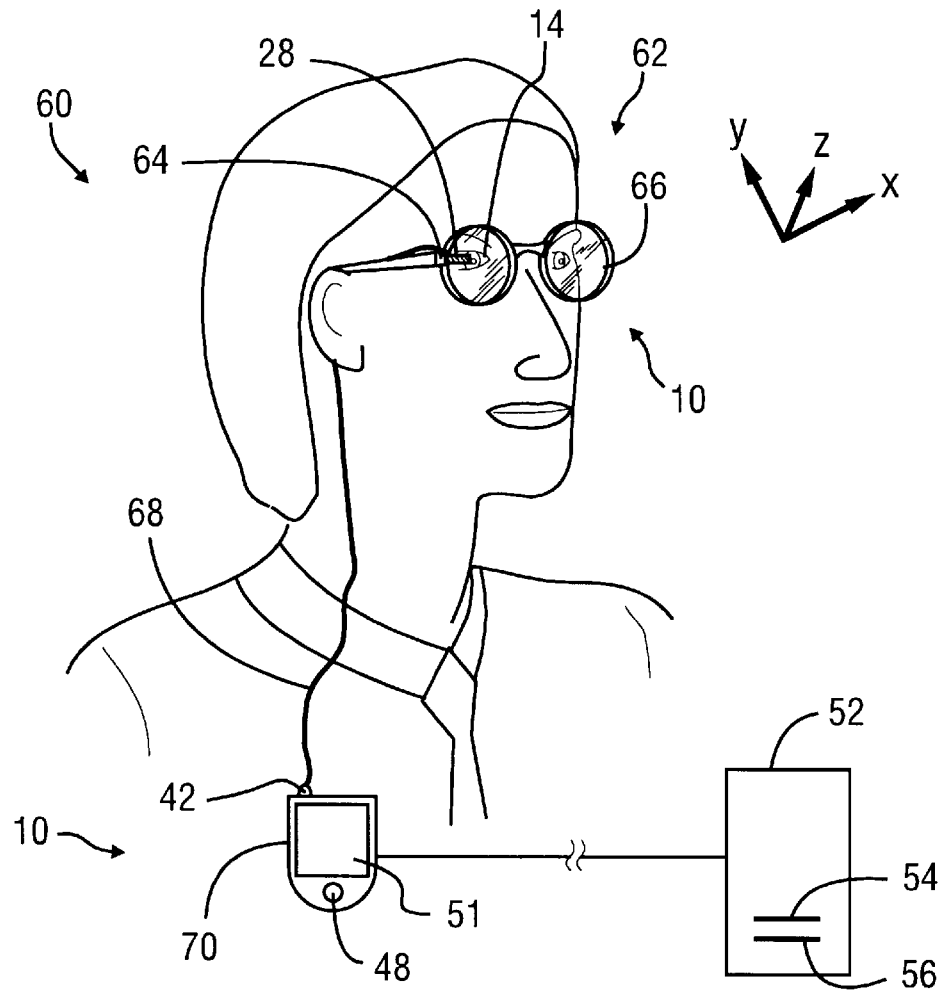
FIG. 6 is a pressure measuring system according to the present invention mounted in part on a patient's eyeglasses.

FIG. 6 illustrates a pressure measuring system 60 which includes an apparatus 10 mounted proximate to a patient. System 60 also includes a remote processor 52 capable of being coupled to apparatus 10. Apparatus 10 is preferably mounted within or proximate to the vessel region. Specifically, apparatus 10 can be wholly or partially mounted within or onto, e.g., the frame of a pair of eyeglasses 62 placeable upon a patient undergoing intraocular pressure measurements. Platform 28 can be secured in moveable relation to a corner 64 of the eyeglass frame. Platform 28, containing emitter 24 and detector 26 is moveable between eyeglass lens and eye 14 in close proximity to and over limbus region 12. If a light-emitting diode similar to that used in Hewlett Packard Model No. HBCS-1100 is used, the entire packaged sensor can be mounted on platform 28 and directed toward limbus region 12 between eye 14 and eyeglass lens 66. Alternatively, if a laser is used, similar to that shown in FIG. 5, reflector 44 and array 46 can be mounted upon platform 28 having a motive source provided via cable 68 coupled to motor 48. Laser diode 42 is preferably placed within a package 70 which houses motor 48, laser diode 42 and a local memory medium 51. A battery (not shown) may be included within package 70 to supply power for operation of apparatus 10.

Figure 8:
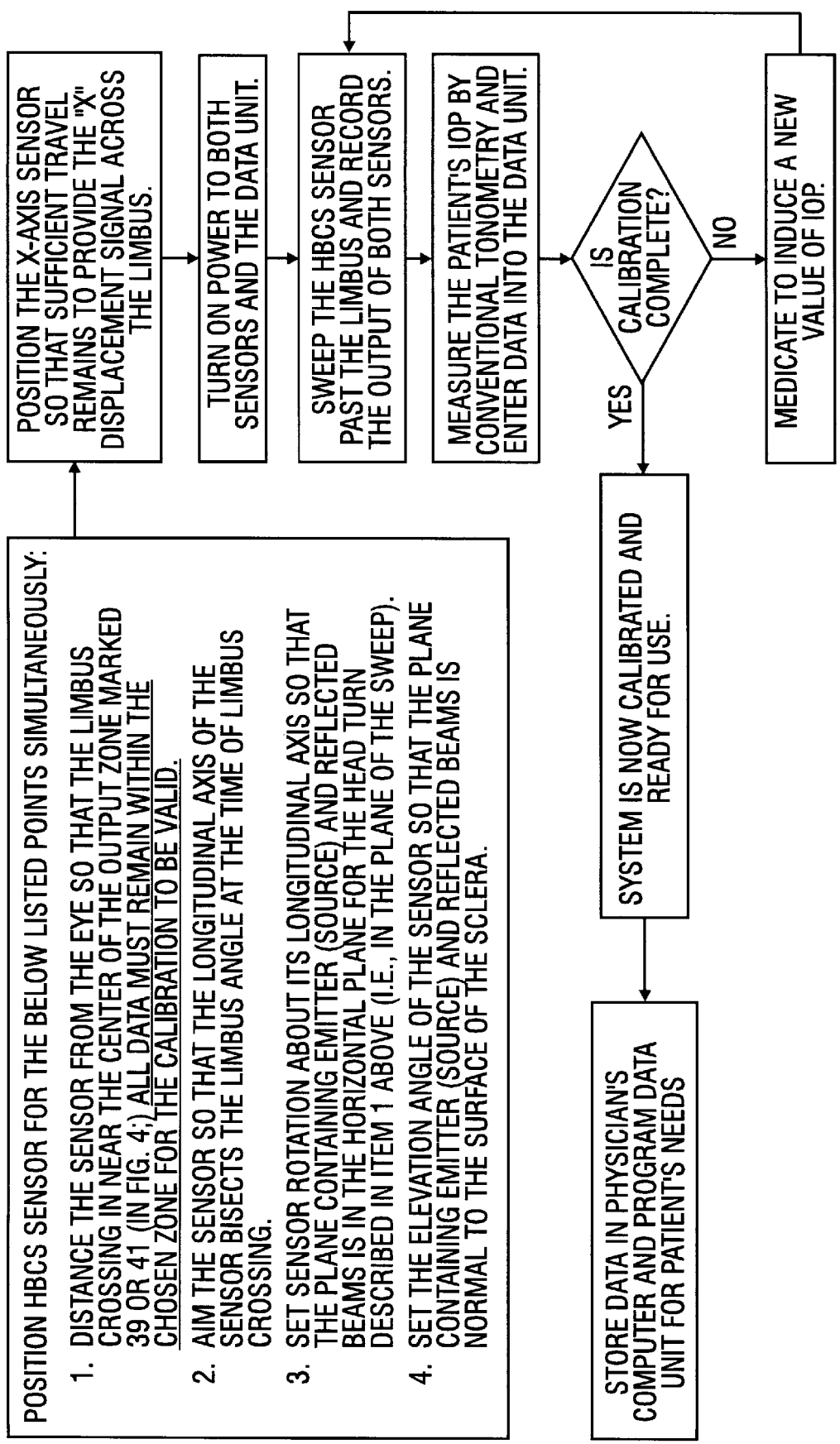
FIG. 8 is a flow chart indicating the procedure for setting up, calibrating, and, in general, readying a system of type similar to a Hewlett-Packard HBCS-1100, with extended focal length, for storing limbus or blood vessel contour signatures in the field.

Cable 68 therefore can provide a rotatable mechanical cable for driving platform 28 as well as an optical wave guide for transmitting laser energy from laser 42. Alternatively, if the optical emitter and detector are fully contained upon platform 28, as shown in FIG. 8, the electrical signals transmitted to the emitter and from the detector are contained within an electrical conductor within cable 68. Thus, depending upon the configuration desired, i.e., whether a laser or LED is used or whether the laser is mounted on platform 28 or on package 70, cable 68 may include an electrical conductor, fiber optic cable, or both. Cable 68 also preferably includes a rotatable cable which transmits mechanical rotation from motor 48 to translational movement of platform 28 and rotational movement of reflector 44.

Eyeglasses 62 can be of common design generally adapted to fit in fairly close proximity to the outer surface or contour of eye 14. Eyeglasses 62, being fairly stationary in relation to eye 14, provides a relatively stable and repeatable positioning tool by which long term and continuous contour measurements can be taken. Eyeglasses 62 can be worn over a period of days, months or even years thereby allowing access for long term intraocular pressure measurements. The operating distance between the platform movably fixed to eyeglasses 62 and eye 14 can vary depending upon various hardware chosen. However, the present design allows contour measurements at varying operating distances anywhere from several millimeters to several centimeters, or even far beyond as in the case of nonphysiological applications.

During each measurement routine, platform 28 can be activated to scan in the X-axis across eye 14 and, in particular, across limbus region 12. Alternatively, it is within the scope of the present invention that scanning can be equally achieved by maintaining platform 28 in a fixed position and naturally moving the eye's focal point along the X-axis. If platform 28 is movable to provide the scanning function, eye 12 must remain fixed in relation to the moveable platform. Thus, the eye can be focused at a fixed point during each scan routine so that repeatable measurements can be taken. A focus point can be provided by attaching a target to eyeglasses 62, whereby the patient maintains fixed eye concentration upon the target during each scan routine. Consequently, each scan presents a scan slice within the X- and Y-axis. Furthermore, providing eyeglasses 62 do not slide a substantial distance down the patient's nose, fixed position along the Z-axis is also maintained between measurement scans.

A first set of values representing the limbus contour signature relating alterations in the reflected waveform angle or intensity (electromagnetic or acoustic) to IOP is stored in a first remote memory medium 54 such as a floppy disk, compact disk, etc. A second set of values representing the calibrated pressure response contour relating alterations in reflected beam intensity or angle to changes in BP is stored in a second remote memory medium 56, similar to medium 54. IOP measurements used in performing the calibration are obtained with a conventional tonometer applied approximately simultaneously with an optical scan of the limbus contour. BP measurements are analogously obtained with a conventional sphygmomanometer. The data obtained during the optical scan corresponding to IOP and BP readings are then stored as calibration data within media 54 and 56. A physician may induce several pressure changes within a patient's IOP or BP to establish a broad range of calibration points.

Signal processor 52 is placed in a remote location from the patient, preferably in a physician's office. Processor 52 includes a computer which can receive downloaded data from local memory medium 51 and compare that data with data stored in remote memory media 54 and 56. The patient can download data from medium 51 through a modem connecting the patient's residence to the physician's office. Alternatively, the patient may visit the physician's office and physically connect output via an RS232, IEEE488, or other port from medium 51 to processor 52. Processor 52 may be a personal computer having external computer bus input and read/write data capability.

Figure 7:
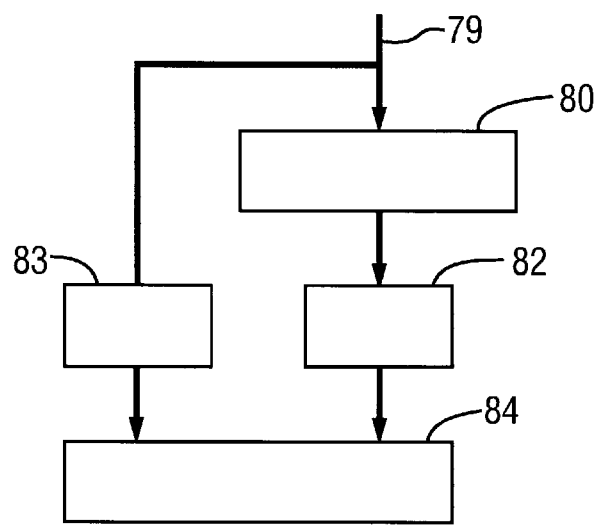
FIG. 7 is a processing flow chart illustrating conversion of contour signature data into intraocular and blood pressure components for patient monitor service.

Digital representations of reflected light beam intensities and positions are convertible to changes in IOP and BP through application of the limbus contour signature and pressure response contour. An example of the conversion process is represented by the processing flow chart shown in FIG. 7. During each scan, IOP measurement data (as stored in medium 51) are entered via input lines 79 to processors 80 and 83. In processor 80, BP waveforms are separated by characteristic wave shape and/or frequency content to be sent on to comparator 82. Thereafter, IOP waveforms routed to comparator 83 are compared therein with the stored digital representation of the limbus contour signature (as stored in medium 54), while BP waveforms input to comparator 82 are compared therein with the pressure response contour (as stored in medium 56) to obtain IOP and BP respectively. Comparison in each case may comprise a table look-up with interpolation of previously correlated IOP or BP data as stored in medium 51 with separate calibrated measurements of IOP and BP respectively, said measurements being made at substantially the same time as the correlated IOP and BP data are taken at the detector (e.g., photodiode array 46). Outputs of comparators 82 and 83 representing estimated BP and IOP respectively are processed for display, warning, storage or subsequent digital processing in processor 84. Thus, as pressure fluctuates throughout a day, week or year, measurements can be checked to determine if pressure calculated from each contour measurement exceeds a pre-determined amount. If so, the patient is immediately apprised of the situation so that he or she can administer medication and/or seek medical treatment. Moreover, processor 52 can provide direct dosimetry information for medications needed to achieve more acceptable pressure readings. By monitoring rapid fluctuations in IOP or BP or long-term trends in pressure, the present invention provides a more convenient and accurate monitoring of pressure so that medication is more effectively dispensed. Timely intervention can then prevent or delay important complications such as blindness (from increased IOP) or stroke (from increased BP).

A functionally identical scheme was used to evaluate this concept by the use of a hand-held, Symbol ™, laser bar-code scanner. The output of the scanner was used to trigger an oscilloscope simultaneously with its beam sweep. The reflections were recorded on a video-recorder approximately aligned with the axis of the reflected beam. Though the sweep of the camera could not be synchronized with the beam sweep, the pulse at the beam crossing the limbus could be observed, on the oscilloscope from the output of the camera's video jack, by manually adjusting the sweep vernier to catch the limbus crossing within the camera's rasterized image. In this manner, the output change at the limbus could be measured within approximately one (1) mm of trace deflection, or to 0.1 V.

A recently slaughtered pig's eye that was pressurized from approximately 4 to 31 mm-Hg by needle and syringe as measured by a Schieotz tonometer was scanned. The pulse generated by the laser beam crossing the limbus was a sharp peak of less than a millisecond duration, but of repeatable character and amplitude. The output pulse heights on limbus crossing varied from 0.5 V at 4 mm Hg, to 1.0 V at 14 mm Hg, and 2.4 V at 31 mm Hg.

Example 2

The following example illustrates the apparatus and method employed in measuring changes in contour and relating such changes to pressure within the eye. Any method of measuring limbus contour of sufficient resolution to define IOP is suitable. This example is provided from initial efforts to identify existing sensors to verify the concept. One such device is the Hewlett-Packard HBCS 1100, a photoelectric sensor with an integral light source of specific wave length, or color, and a detector that measures the light reflected from the target through an integral lens, designed to optically couple emitter and detector. This sensor is used to read digital bar codes, measure thickness of sheet materials, or detect the presence of a sheet in a feed mechanism, etc.

Preliminary Measurements on Eye Models and Human Eye

This apparatus was tested initially using a Hewlett-Packard HBCS-1100 sensor. It was used with precision sweeps past the "limbus" of an acrylic model of a human eye; and with manual sweeps of the beam past the limbus of an actual human eye. The data from the output of the sensor in sweeping the model eye were recorded on one axis, with the output of a sweep position potentiometer on the other axis, of an X-Y recorder for three successive sweeps with slight repositioning of the initial point between the tests. The results were three separate traces, displaced slightly, that tracked each other with nearly perfectly parallel separation. There was a reversal, or notch, at the instant of crossing the limbus that was identically repeatable. Under microscopic evaluation it was determined that there was a scratch in the plastic at the limbus that gave the notch. This scratch was visible only under magnification. Subsequent inspection on an optical comparator, at 40× magnification, indicated that the scratch was of less than 1/10,000 (0.0001) inch in depth, yet it produced a trace deflection on the x-y recorder output of over ½ inch. The low intensity LED beam also was passed over the limbus of the human eye and the output was qualitatively observed on an oscilloscope with large scale deflection. The output was reproducible at the limbus crossing.

The HBCS-1100 is not ideal for direct application due to its short focal distance of less than 0.1 inch that would require that it be mounted too close to the eye for practical use. However, the aspheric lens may be modified to longer focus (Zmax) distance. While this is generally an expensive and time-consuming process, a similar sensor, with integral and sealed emitter/detector as a single unit, is satisfactory for the described application. This unit is necessarily fixed in its optical relationship and is, therefore, adaptable to change in prescription for patient's need only by Z axis placement of the unit or angular alignment of the optical axis.

FIG. 8 is a flow diagram that illustrates a setup, calibration, and data acquisition scheme for a sensor of the same type as the HBCS-1100, but with a longer focal length lens. The integrated assembly of this device facilitates the installation and adjustment of the unit, but limits flexibility.

Figure 9:
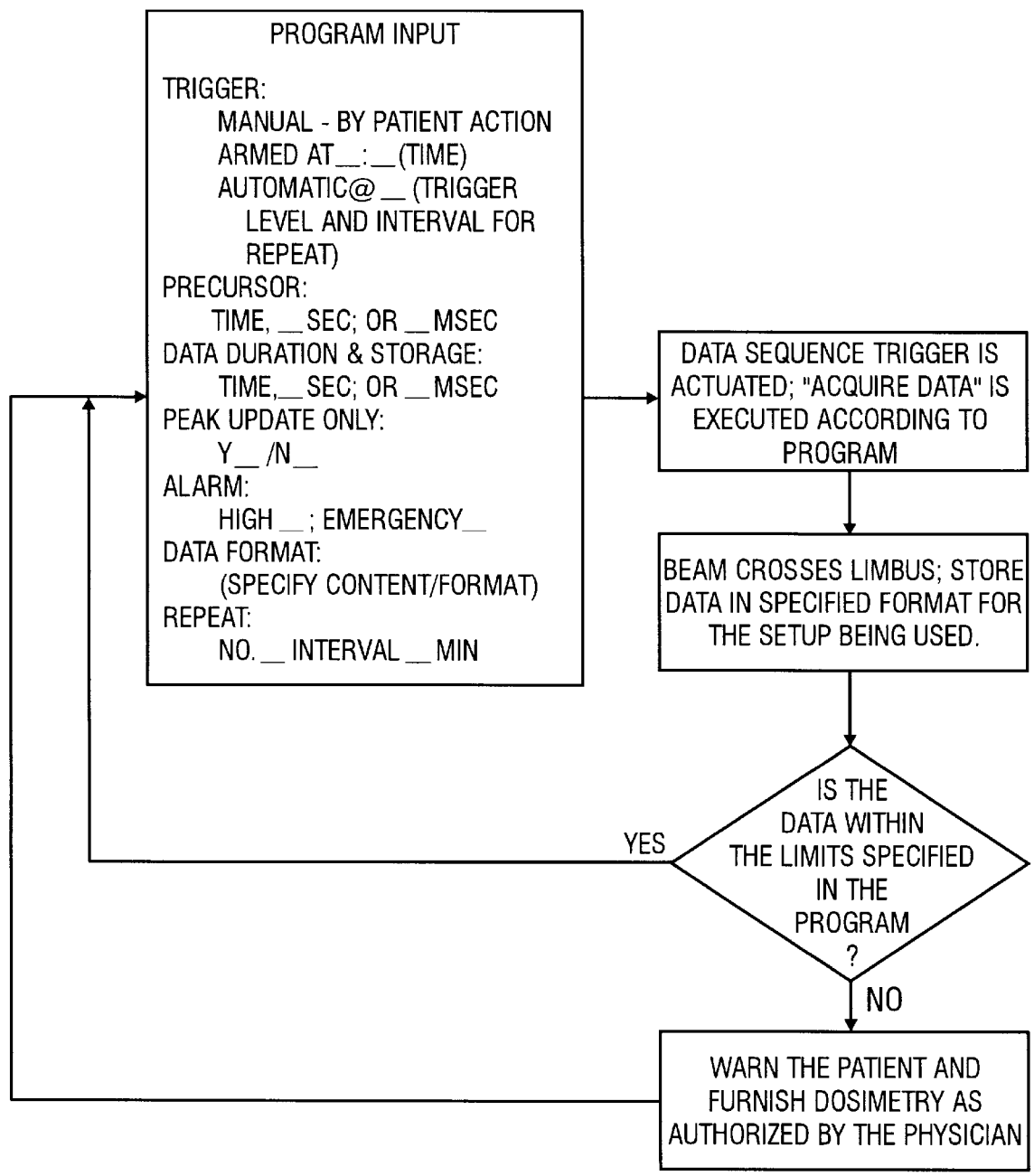
FIG. 9 is a flow chart typical of what might be set up in the data unit to tailor a system for a given patient.

It may be desirable to employ a separate sensor for the measurement of x-axis displacement as shown in FIG. 3, since the lens somewhat masks the effect of the discontinuity at the limbus with optical interference. This probably could be overcome with additional study of lens characteristics. As shown in the flow diagram of FIG. 8, the first task is to set the HBCS type sensor in position relative to the eye for producing the best possible signature from limbus crossing. The x-axis transducer, which may be a linear potentiometer, or a DCDT (direct current displacement transducer, a differential transformer with solid state oscillator and demodulator, etc.) is also set up to define that component of the contour profile. The data unit will include the required signal conditioning for both sensors along with the power supply for all elements in addition to that shown in the flow diagram FIG. 9 for the patient's pocket data acquisition unit (hereinafter the "data unit") function. The flow charts of FIGS. 8 and 9 show steps that may be taken to calibrate such a system for IOP measurement and ready it for data acquisition in the field. The parts for accomplishing the items in both of these figures are of common usage in the field and may be accomplished by numerous combinations of components by one skilled in the art.

Example 3

In order to obtain a system that may be specifically tailored to a patient's specific requirements, a system with greater flexibility is required. Since IOP measurement is a function of reflections from essentially discrete spherical surfaces, beams incident the sclera near the limbus will give discrete reflections as the eye rotates so that the limbus crosses the fixed beams. These beams may be positioned in placement and angle to produce desired incidence. Additional flexibility for prescription is afforded by a separate photodetector that may be positioned independently of the emitter source.

Description of this embodiment is simplified by considering a single beam source, initially. This is not overly simplistic since such a system is capable of making useful measurements, in the physician's office as well as in patient use and, in fact, is expected to be the preferred embodiment for most patients. In this embodiment, as calibration signals are recorded at several values of IOP, they also are recorded at several angles of elevation of the line of sight for each IOP.

Single Beam Example

Figure 10A:
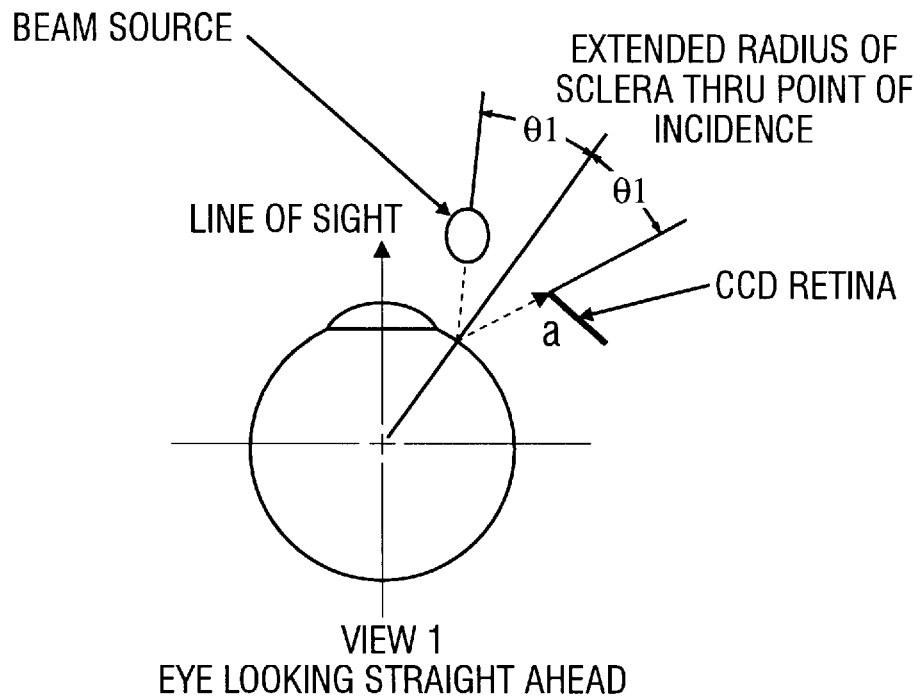
FIG. 10 is a sequence of sketches illustrating key points in the generation of data by a single fixed-beam sensor system with electronic retina.
Figure 10B:
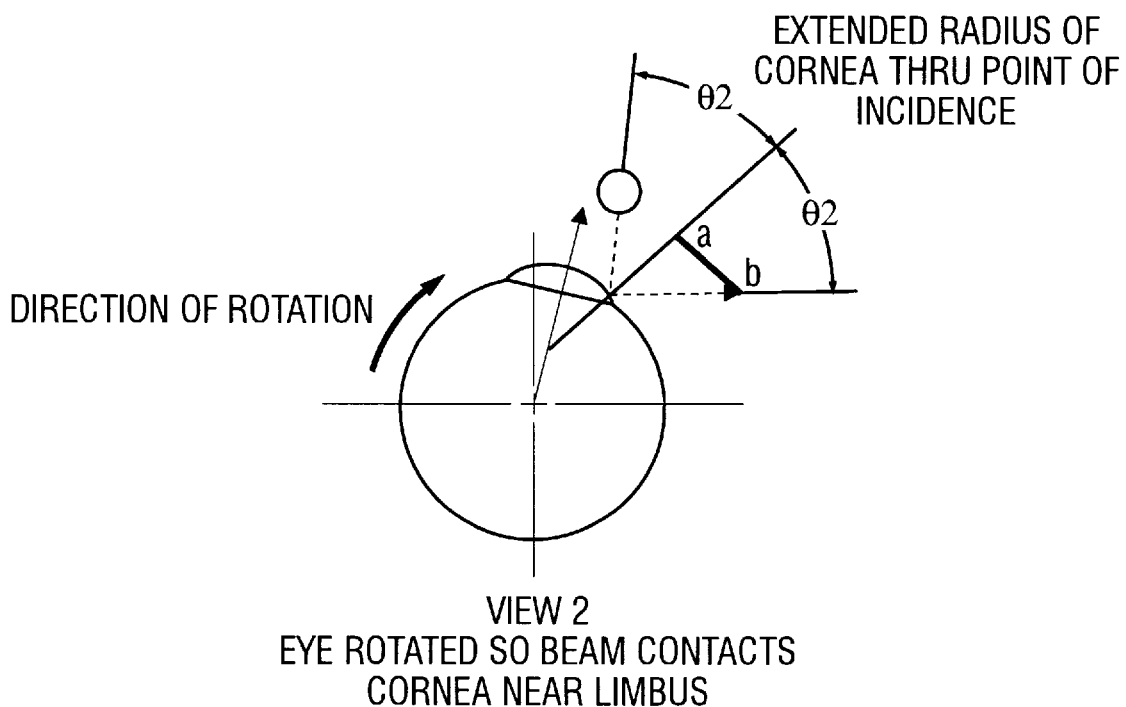
Figure 10C:
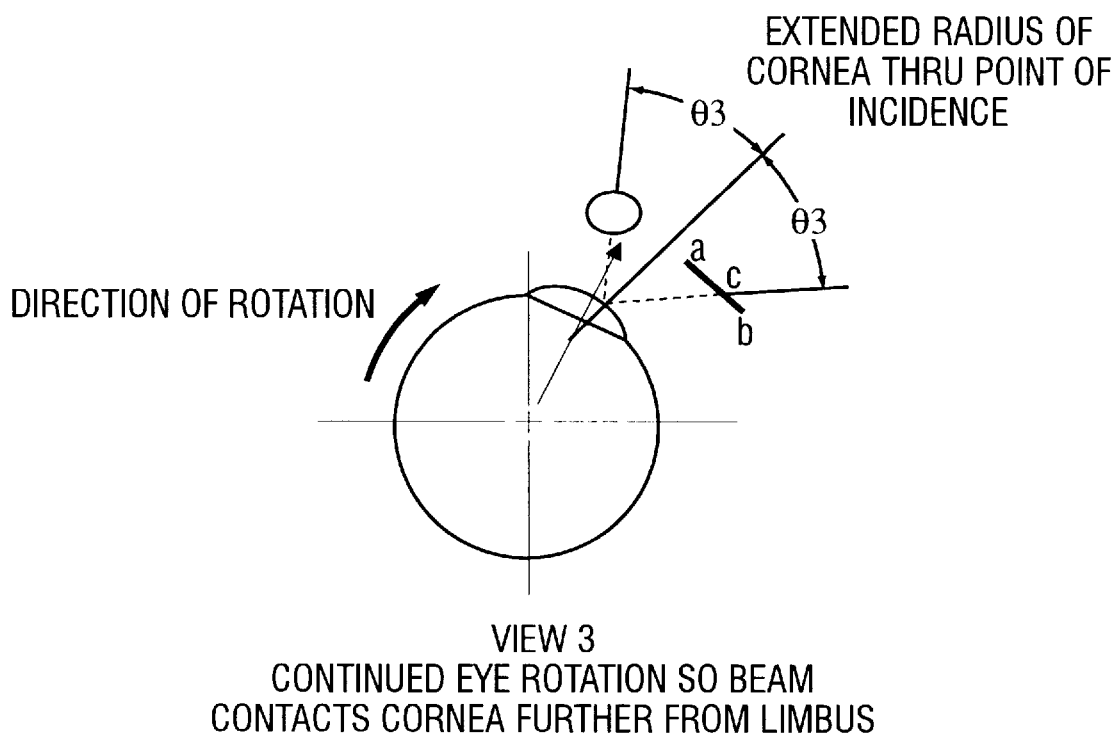

FIG. 10 shows a system with a single beam in fixed relation to the eye's socket (center.) The system is configured by the physician's prescription to meet the patient's needs; and this figure shows a typical setup.

The lateral axis of the eye in FIG. 10 is horizontal and in the plane of the paper. The view looking down this lateral axis is not shown since it is illustrated in the three view sketches of subsequent discussion in greater detail. The beam path, and its reflection, lie in the horizontal plane of the eye's symmetry so that both incident and reflected beams shown in this figure are in the plane of the paper. For this idealized example, this array would give a straight, horizontal trace over the surface of an electronic sensor that, in effect, is the "retina" of the device (hereinafter referred to as ER for electronic retina).

View 1 of FIG. 10 shows the eye looking straight ahead with the beam adjusted to reflect off the sclera and onto the ER at point "a". The angles labeled $\phi 1$ represent the angles of incidence and reflection relative to the surface of the sclera. To acquire data for either calibration or data acquisition consistent with this scheme of components, the eye is rotated substantially about the vertical axis of the sclera. This rotation may during routine motion of the eye be directed by an image moving in plane, in front of the eye, or by a maneuver performed by the patient in rotating his head about a vertical axis in opposite sense to the desired eye rotation. The resulting involuntary rotation of the eye is a motion that is easy to reproduce by both sighted and blind patients. Since the sclera is nominally spherical, and the eye rotates about the center of the sclera, there is little deflection of the beam prior to its contact with the limbus except from the surface roughness of the sclera.

In View 2 of FIG. 10 the beam has just crossed the limbus onto the cornea with the result that the beam angles of incidence and reflection are now at $\phi 2$. The extreme deflection of the beam relative to the ER, to point "b," occurs here. This maximum deflection of the beam, from a to b, is the analogy for the measurement of IOP; the axis defining incidence and reflection has shifted from sclera to cornea.

View 3, FIG. 10 illustrates that beam deflection to "c," as the eye continues to rotate clockwise is such that $\phi$, now $\phi 3$, is diminishing. The increased rate of beam deflection per unit of eye rotation is due to the shorter radius of the cornea (relative to that of the sclera), that governs beam reflection at this orientation.

In the real case, the limbus is not purely angular, and the actual step from a to b is "softened" by the slightly radiused contour of the limbus. The beam path, recorded by the output from the ER, may be reduced to IOP units; either directly, from a stored calibration table or function in the patient's data unit; or indirectly, where the data is stored on portable medium in the data unit for subsequent comparison to calibration data in the physician's office. Medication is authorized according to prerecorded instructions in the data unit, or by telephone, modem, pager, etc.

Figure 11:
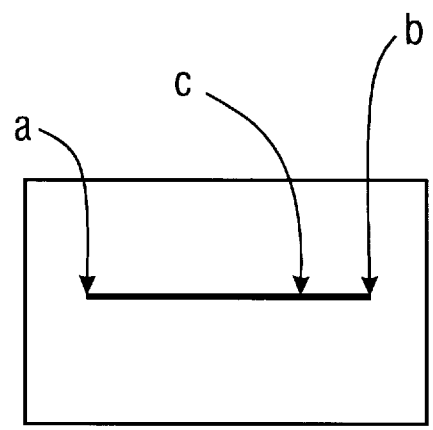
FIG. 11 is a diagram showing beam path over the electronic retina of a single beam system as the beam crosses from sclera to cornea.

FIG. 11 shows the ER with the points labeled as described above.

Figure 12:
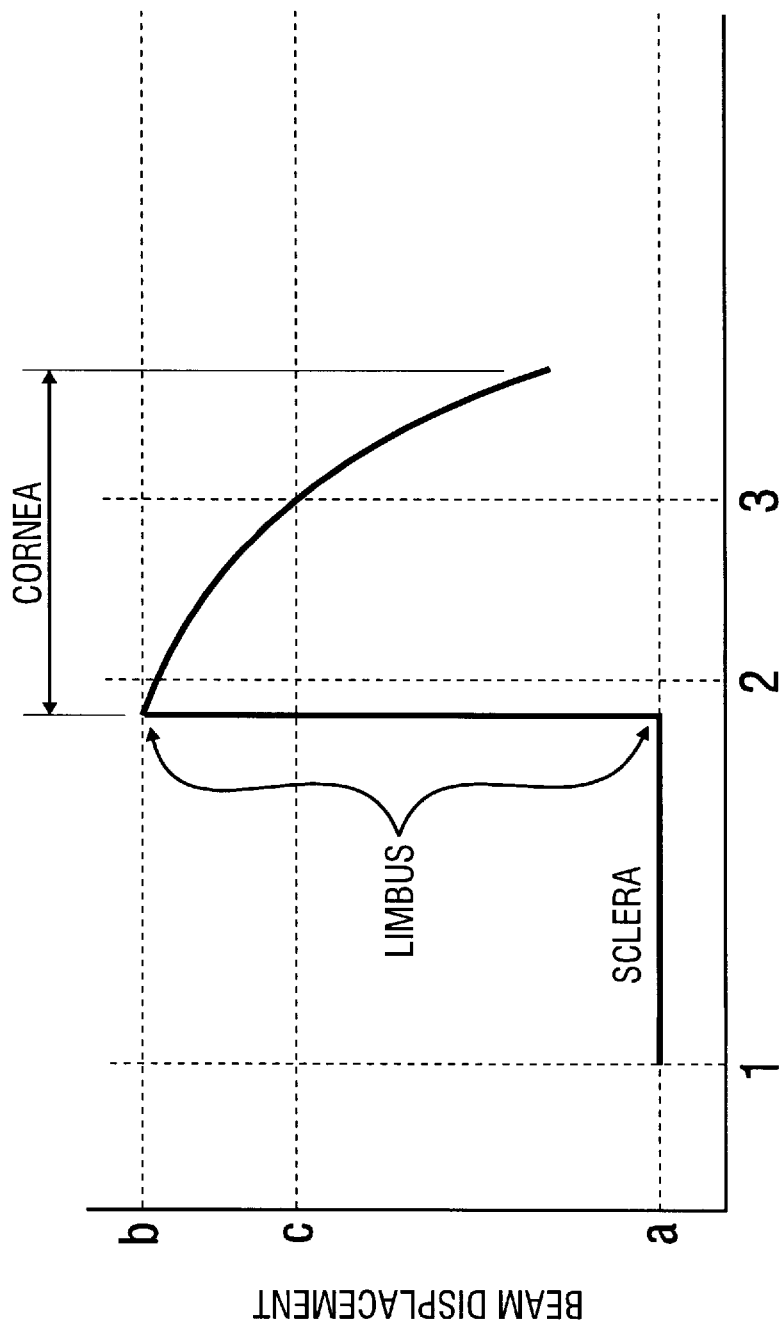
FIG. 12 is a sketch showing the signal generated from a single fixed beam crossing from sclera to cornea as a function of rotation angle, or time, during a typical data sequence.

FIG. 12 shows typical output from the sensor, giving beam displacement relative to rotation of the eye; The deflection from a to b is related to IOP by the calibration data. The deflection of the beam in the vertical plane is a function of the elevation of the angle of sight, making each image step at the limbus and its angularity uniquely representative of both limbus contour and elevation of line of sight.

Figure 13A:
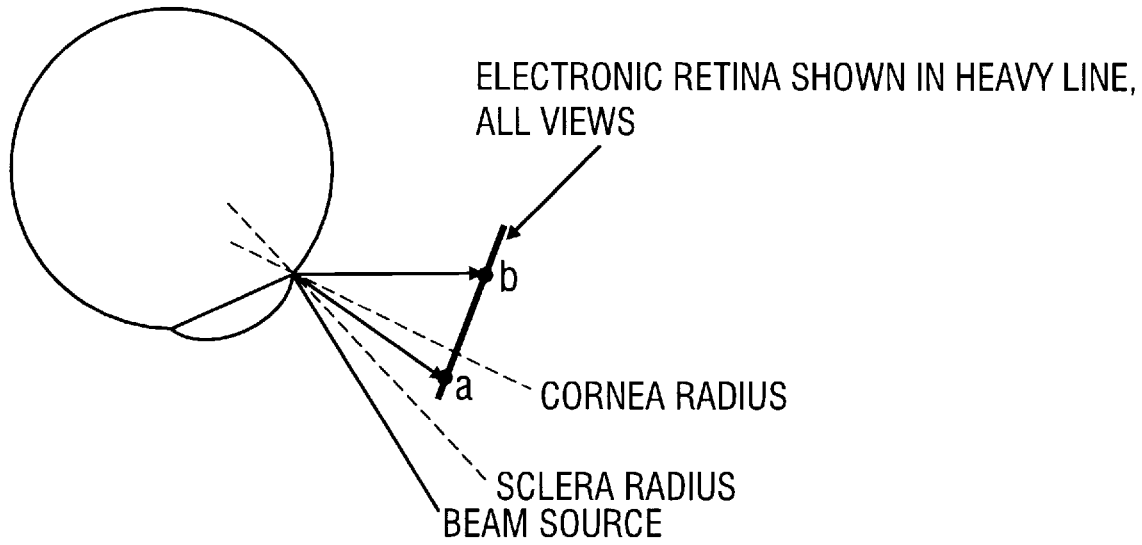
FIG. 13 illustrates the generation of a vertical component of deflection of a single beam reflection, onto the electronic retina by a specific angle of elevation.
Figure 13B:
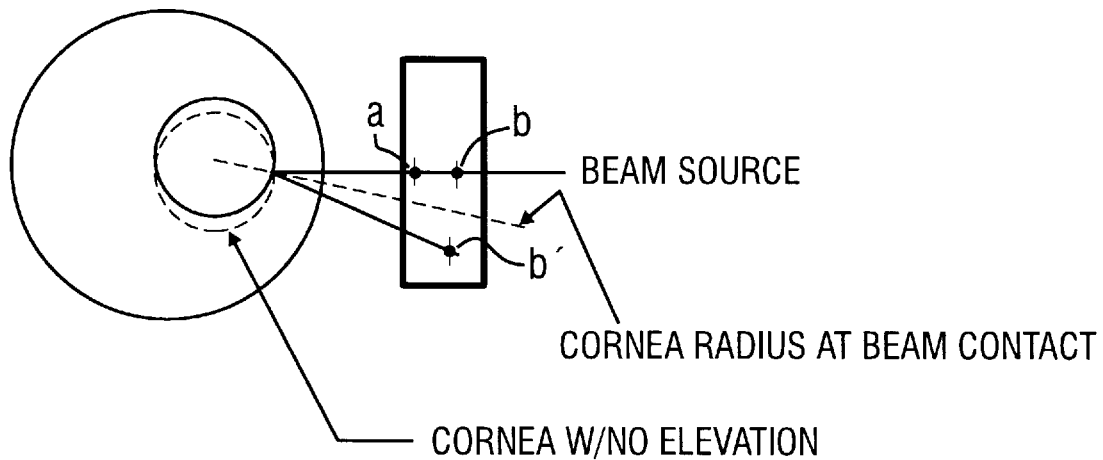
Figure 13C:
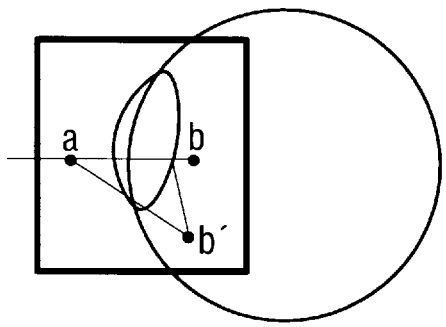

FIG. 13 shows the effect of approximately 5° of elevation of the angle of sight on the data. The corneal outline shown in dashed line in the front view gives horizontal line of sight; all in solid line is elevated. The normal to the cornea (its radius since it is spherical) establishes incidence, and the result is that the beam is reflected from a to b'. The angle between a to b' and the axis of the ER (a to b) is proportional to elevation angle. The signature on the ER, then, consists of the step from a to b' that is proportional to IOP; and the angle of a to b', proportional to elevation. The "softening" of actual limbus contour diminishes the slope derivative at the limbus and provides a path over the ER of discrete path and longer duration, making tracking easier than if it were a true discontinuity. Note that if the cornea and sclera are truly spherical there is no need to measure elevation for separate entry for calibration.

Figure 14:
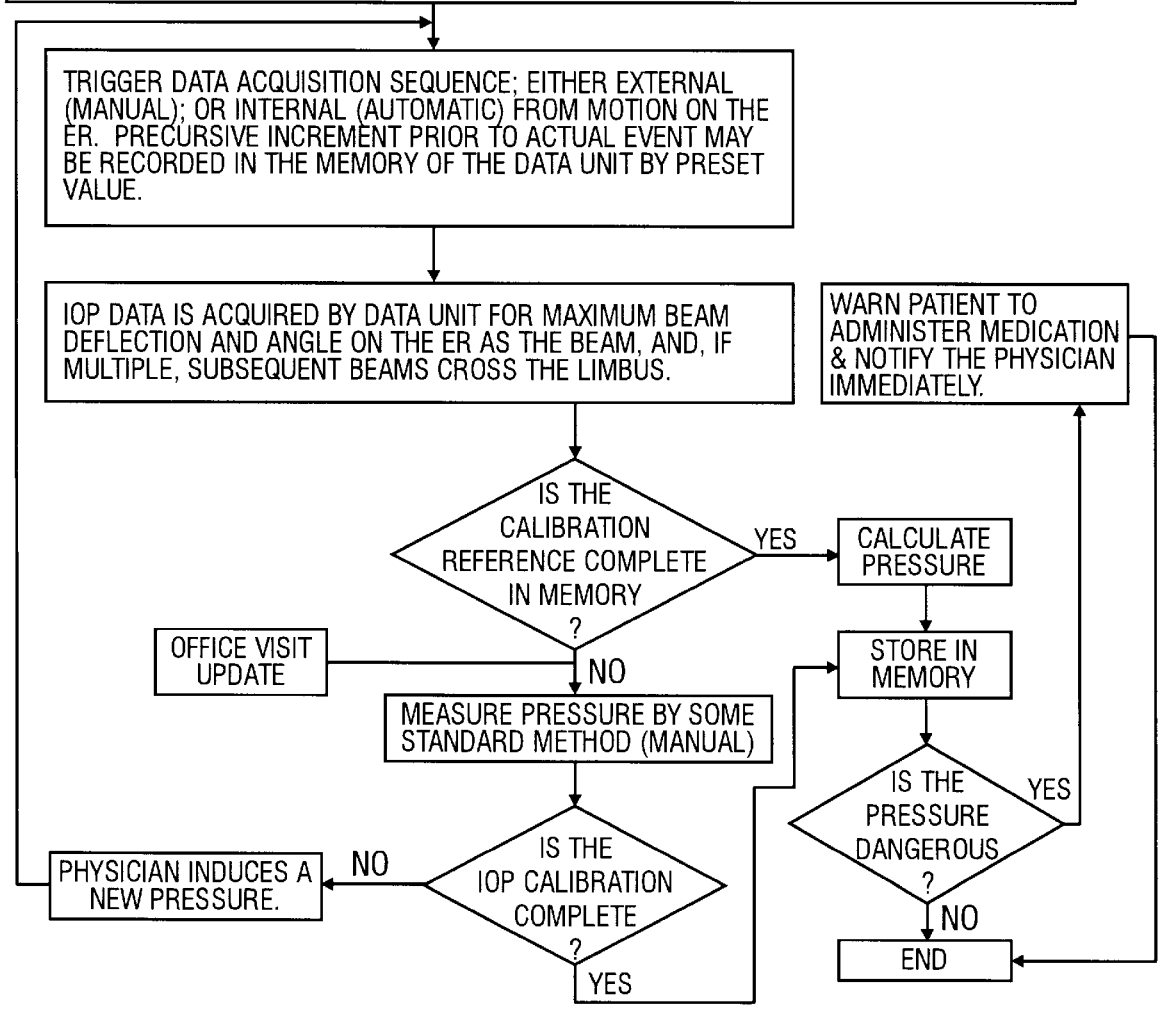
FIG. 14 is a flow chart illustrating the setup, calibration, and field data acquisition of signals from discrete beam systems with electronic retina.
Figure 15A:
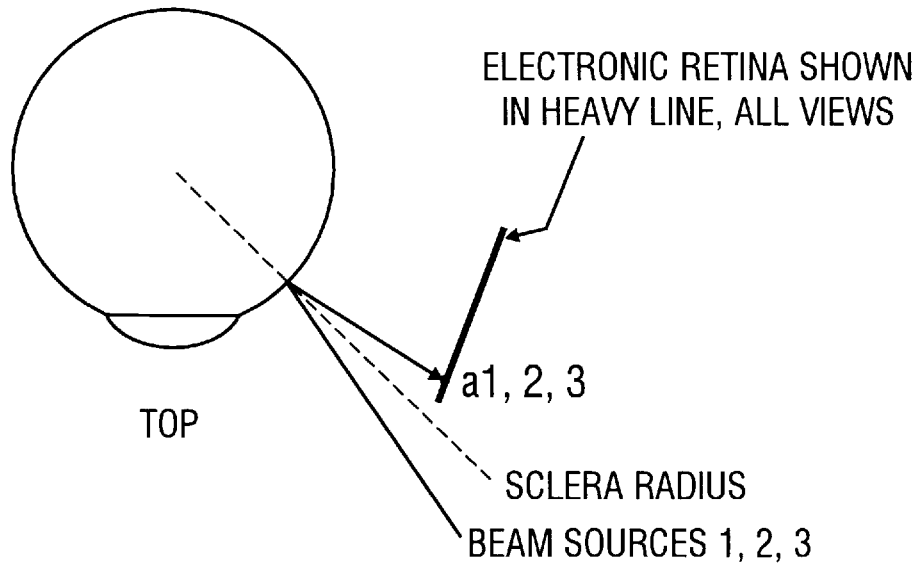
FIG. 15 views 1,2,3 are a series of views that illustrates the addition of sensors to extend coverage of a greater arc-length of limbus contour and/or increase the range of allowable elevation angles for field data acquisition.
Figure 15B:
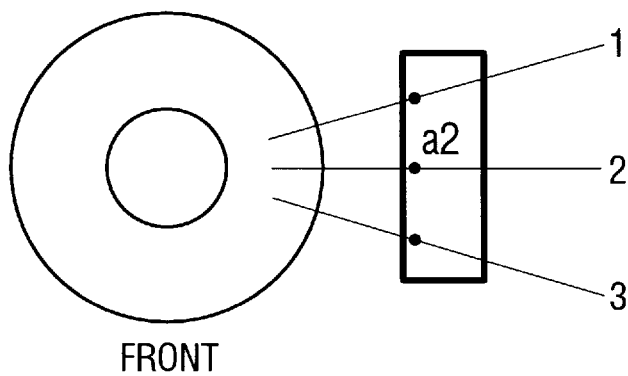
Figure 15C:
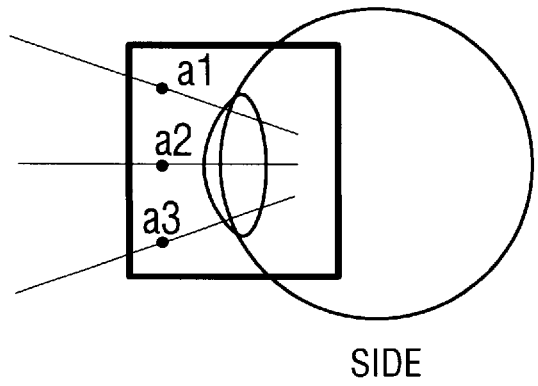
Figure 15D:
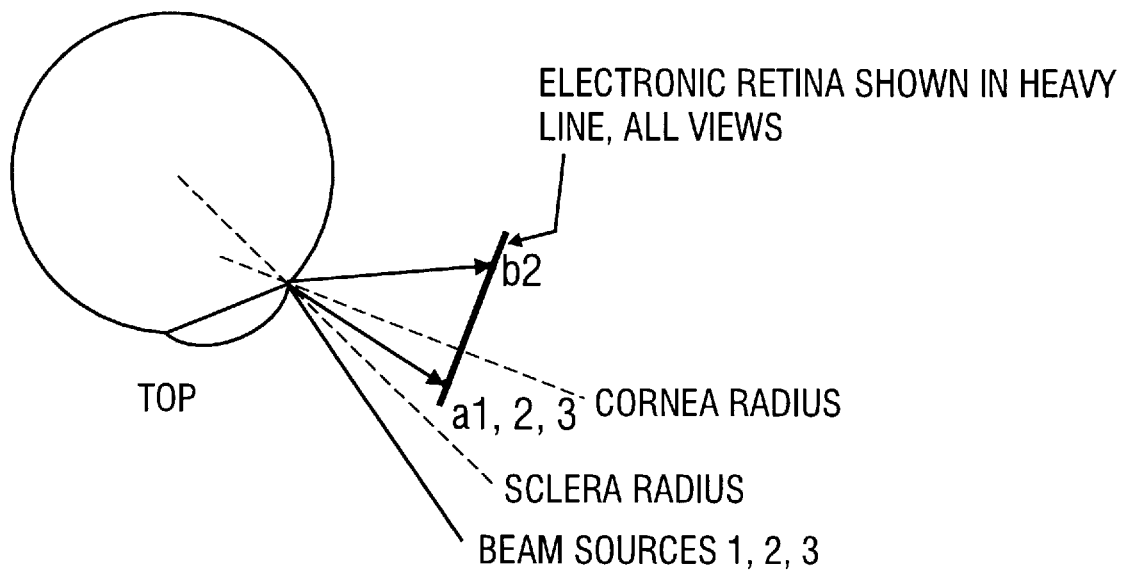
Figure 15E:
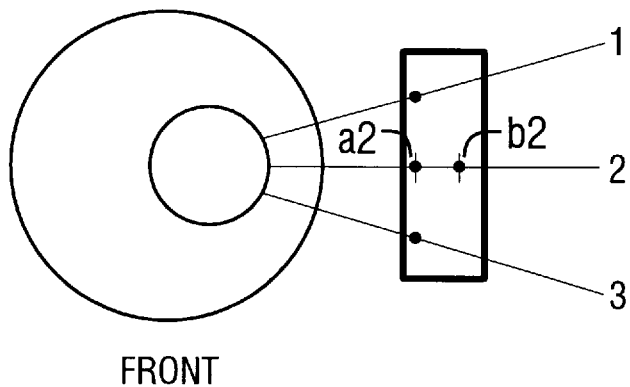
Figure 15F:
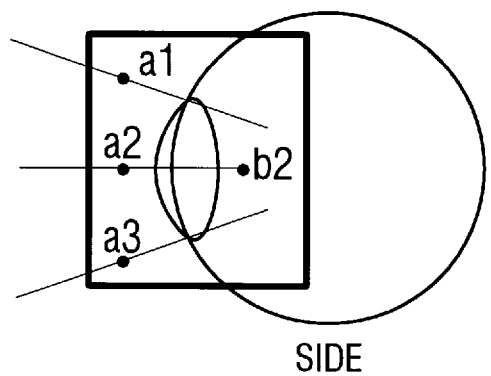
Figure 15G:
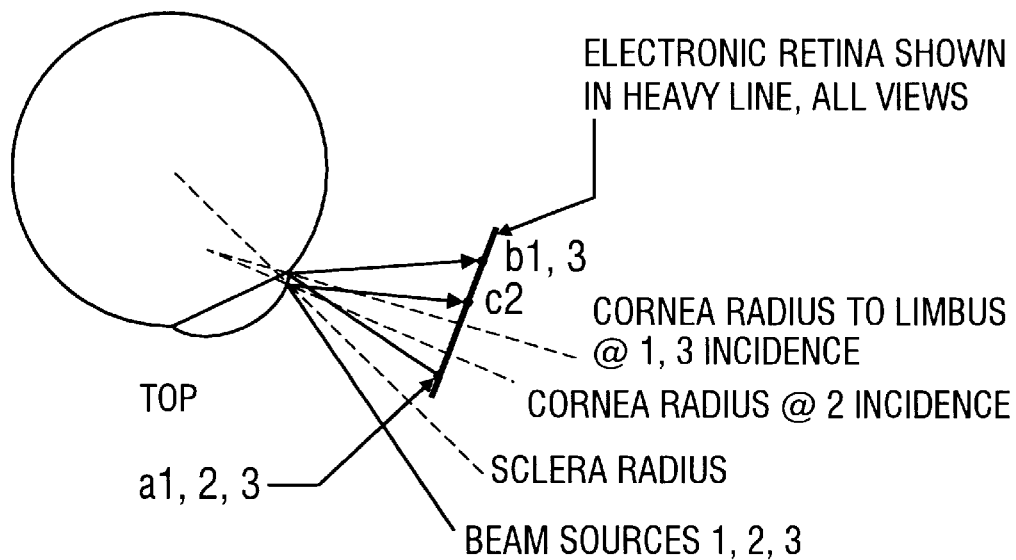
Figure 15H:
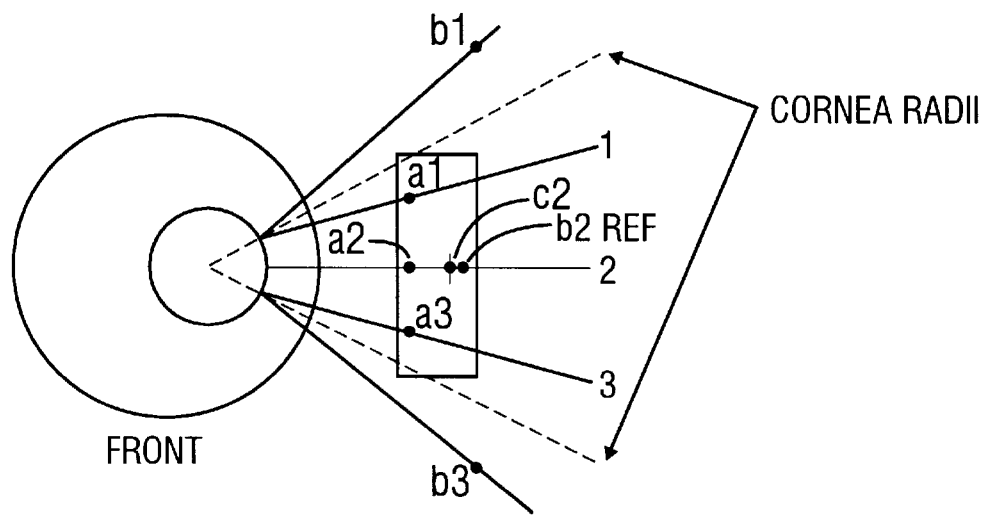
Figure 15I:
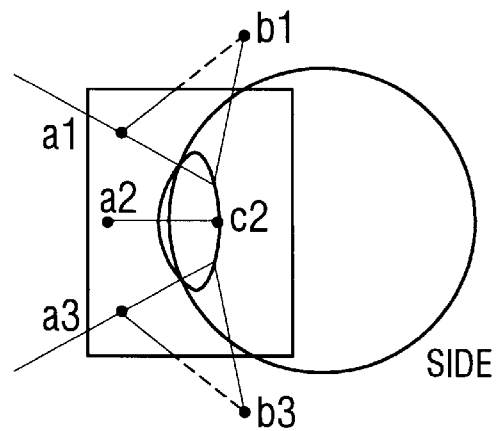

The only difference between calibration data and that for actual patient monitor is that, for calibration, data are taken in the physician's office at several levels of IOP induced, by medication, and with "conventional" tonometry used to measure actual IOP's against which beam deflection is compared. This gives calibration curves of IOPs as functions of peak beam deflection and angularity. FIG. 14 is a flow chart that illustrates a setup, calibration, and data acquisition scheme for systems with discrete beam sources and ERs that use the deflection at the limbus discontinuity as the primary transduction principle. FIG. 14 is valid for both single beam and multiple beam systems with the only difference being the number of sources aimed at the eye's surface.

This single beam system was tested by using an Apollo MP-1600 laser pointer through a pin-hole aperture for beam sharpening; again, with a pig's eye for analysis. The pressure was from a reservoir connected to the eye by IV connection, and the pressure equivalent in mm-Hg was set relative to the pupil, with water column height. The optical arm from the eye to a sheet of graph vellum that served as ER was approximately 3.5 in. In taking the data, the beam was swept past the limbus by a vernier on a precision height gage. The angle of incidence was estimated at 10–15° off normal to the sclera. The resulting data are shown below:

| SINGLE BEAM DATA2 | |
| --- | --- |
| IOP P-mm-Hg | Trace Deflections - mm |
| 0 | 36 |
| 10 | 63 |
| 20 | 95 |
| 30 | 115 |

Example 4

The single beam method will handle the majority of patients' needs. Multi, or swept beam devices are feasible also. One reason for the multi-beam embodiment is in the case where there is substantial variation of limbus contour over the small arc where the contour signature is to be taken and the definition from a single source is not discrete; Another is an increase in the range of the angle of elevation of the line of sight for automatically acquired data. These points also are true for the inversion case where a single beam is swept as in a bar-code scanner or Example 2 so that it touches or crosses the limbus with the eye stationary.

Multi-Beam Systems

FIG. 15 shows a three-beam configuration that produces reasonable signatures over a broad range of elevations of line of sight. The principle, illustrated in FIG. 15 shows progression through three sets of sketches as the eye rotates so that the limbus crosses the beam array; the array being fixed in relation to the eye socket. The top view of View 1, FIG. 15, shows that the beams for this example are aligned at an angle of incidence relative to the radius of the sclera so that the reflections fall on the ER as shown. It is emphasized that specific geometry and number of beams will be by prescription of the physician. In this example, three beams are directed normal to the surface of the sclera as seen in the view looking directly into the cornea, with the result that the reflections are at points a1, a2, and a3 on the ER. These designations signify:

1. The letters a, b, or c mean that the reflections are from sclera, the corneal edge of the limbus, or the cornea surface, respectively.
 2. The numbers 1, 2, and 3 indicate the specific beam causing reflections shown in the sketches.

View 1 is the initial setup and the reflection positions remain essentially constant, except for deflections over blood vessels or other roughness of the sclera, as the beams move over the substantially spherical sclera when the eye rotates in its socket. As the limbus contacts beam 2, as shown in View 2, the point of reflection on the ER jumps from a2, to b2, as the spherical surface governing reflection shifts from sclera to cornea at the limbus. The top view of View 2 illustrates how the angles of incidence/reflection shift as beam 2 reaches the corneal side of the limbus. Due to the circularity of the limbus in the front view and the linear array of beams incident the sclera, beams 1 and 3 are undeflected. The deflection from a2 to b2 is the primary analog for measurement of IOP.

As rotation of the eye continues further in the same direction, as in View 3, beams 1 and 3 contact the limbus at a1 and a3, and are reflected to b1 and b3 as shown in View 3. In this example they are reflected beyond the surface of the ER, however, the path angles are preserved, confirming angles of reflections that result from off-center contact with the limbus. Their symmetry confirms normal contact between beam 2 and the limbus; hence "zero" elevation angle. Deflections from a1 to b1 or a3 to b3 are, or would be, separate and corroborating measures of pressure to that of beam 2. (Beam 2 would be skewed, had there been a change in elevation, and either b1 or b3 would rotate so as to move onto the ER.) In View 3, beam 2's point of incidence has risen on the cornea, with the result that it is now reflected to c2.

Beams 1 and 3 may be kept on the ER by geometry changes in the physician's prescription for the apparatus. Two examples of prescription change to keep the reflections on the ER are offered here: first, the angles between beams as seen in the front view of View 1, which are normal to the surface of the sclera as shown, may be increased (holding the central beam and points of incidence fixed) to give an increasing angle of incidence in this plane, hence, moving the a1 and a3 positions closer to a2. Also, the pitch, or spacing between beam points of incidence, may be reduced by reducing the angle between them, while keeping them normal to the sclera, to accomplish the effect of moving a1 and a3 closer together. Regardless of details of the setup, the measured response of the system at various IOPs affords the calibration.

Example 5

The prescription for the patient's system may be determined in the physician's office by a system similar to those of FIGS. 10 or 15, but with adjustability and verniers or other scales to show adjustment details. Scans are made after the apparatus has been set to the physician's satisfaction, to verify the function of the final configuration of the adjustable system whose settings are used to define that to be prescribed for the apparatus to be used in the field.

Calibration

The calibration is accomplished with the patient's personal apparatus of either separate or integral (to the eyeglass frame) type, and consists of sweeps of the eye past the beam array at several values of IOP over as broad a range of IOPs as it is practical to induce at the time of calibration. Separate refers to a system that is packaged separately from the eyeglass frame which may be placed over the eye with glasses removed for data acquisition. This allows for opaque seal to exclude ambient light from interference with the proper function of the apparatus, but also eliminates automatic triggering.

The calibration procedure is never complete. Data from high pressure "events" in the physician's office will be recorded, verified by conventional tonometry, and entered into the calibration data file for calibration extension at every possible occasion.

A curve, of reasonable range may be generated, in relatively short order if a high pressure episode can be used to produce several levels of IOP by successive medication. Precise measurement of IOP during scan for record is made by a precision unit such as an applanation tonometer, and scans at several values of elevation may be made to establish the correlation between angularities on the ER, and the values of deflections of the beams that are proportional to IOP. This method is not intended to replace precision measure of IOP; rather, it is a method of detecting high pressure episodes, for correlation to the events that cause them. The device is sufficiently quantitative that medication in proper dosage may be taken in time to prevent physiological damage. This invention is sufficiently quantitative to document diurnal variations, resulting from patient routine, so important to treatment of glaucoma. Events may be cataloged and correlated with other patients with the same type of glaucoma to aid treatment. It is difficult to overdose a patient with pressure reducing drugs, therefore, significant reduction of blindness will result from this self-monitor method of determining overpressure and proper medication.

IOP measurement by conventional means, with correlated sweeps are taken at each office visit as part of the patient's history; and the calibration function is verified and expanded on a continuous basis. Changes in calibration are extremely important and give advance notice of physiological change. Excessive IOP, in addition to causing damage to the optic nerve, also can cause other permanent change in the eye. This is similar to the effects of engineering materials being stressed beyond their proportional limit, with resulting permanent distortion. This invention offers the ability to detect and track such damage and to suggest therapy and changes in patient routine to minimize deterioration.

For final calibration the resulting peak deflections from limbus crossing are tabulated against induced IOPs' and the deflection and angular signatures are analyzed and stored as calibration functions. The values of induced IOPs are determined by conventional tonometry and entered into the patient's data unit and/or physician's computer, manually.

If the head is kept near vertical the rotation of the eye is restricted substantially to rotations about the vertical axis. The elevation angle modifies the angular deflections of the beams that are repeatable functions of contour, hence are measures of IOP. Recordings of these signatures at the different induced pressures and/or elevations produce the calibration reference.

Example 6

The acquisition of data with this unit should be automatic, if possible, particularly for the case where the diurnal variation of pressure is desired. This is so that the pressures will be little effected by having to think of, and manually prepare for, data capture. If preparation is required, the patient's response tends to be influenced by the act of triggering the data. In general, the data are recorded directly in digital format as is consistent with the devices that are typical for the ER. Several methods of triggering the recording of data may be used as has been previously illustrated in FIG. 9.

Data Acquisition

Data from the ER may be monitored on a continuous basis so that when the triggering event occurs, such as from the deflection of a beam to indicate IOP beyond a programmed limit, that data will be recorded in the data unit. In addition to recording, the unit notifies the patient by sound or vibration that the data has exceeded program limits and that he needs to take appropriate action. Triggering may be effected by several methods which include, but are not limited to:

A. Continuous monitor, of a "window in time" (fixed interval), with triggering afforded by deflection of a beam on the ER in a manner similar to that for an oscilloscope. The "width" of the window allows storage of a precursive time increment (i.e., prior to triggering) to insure capture of the entire event.

B. Manual actuation of a switch to "set" the trigger, followed by head turn to induce involuntary eye rotation; this is useful in recording events where the patient notices something that indicates he should record his IOP. Automatic disablement of this feature generally will be programmed to prevent interference with a previously triggered event, being recorded, that the patient is not aware of, though a "recording" light will be included on the data unit to indicate that recording is in progress. This disablement also may be set to vary "window width," to restrict recording time and conserve memory.

C. Data may be triggered by combinations of programmed timing in the data unit to arm the trigger to record the next limbus crossing as sensed by the discontinuous step on the ER, or by notifying the patient by something, such as a vibrator that it is time to manually record data. Automatic triggering is helpful in establishing diurnal pressure variations for the patient. Data may include date and time as part of the format. "Peak memory" update may be used to capture and store extremes of pressure excursion triggered by routine eye motion that surpasses previously recorded deflection.

D. The simplicity of data format required to store IOP defining information (beam deflection and angle) makes feasible the continuous acquisition of data for 24 hours or more.

The beam sources should be as independent of ambient spectra as possible to minimize background interference for the integral unit. This is inherent in the separate apparatus since background is eliminated. While it is desirable to maintain a cosmetically pleasing configuration for the integral unit, it may be that a sealed or shaded "goggle" must be adopted to control ambient interference. It is possible to sample ambient spectrum as part of each data set and apply appropriate correction, but this complicates collection, reduction and correction of the data significantly. Each beam may be given a different character (such as color) for identification. The separate unit has no background clutter, of course.

Example 7

For the integral system, the data unit may be kept "at the ready" continuously, or "armed" by a separate timing function, and triggered by signal characteristics and conditions that may be either external to, or continuously monitored on, the ER itself. In this way the diurnal variation of IOP during the patient's routine may be determined for his treatment in a manner that is impossible under monitor by conventional tonometers.

Data Storage, Reduction and Processing

Once triggered, analog or digital data from the ER is recorded by the data unit to store the paths of beam reflections as the beam crosses the limbus. An example here is data from pixel by pixel illumination as a beam travels over a charge coupled device (CCD). The signature of a limbus arc segment may be constructed from the signatures of multiple beams to characterize asymmetric corneal distortions in conjunction with three dimensional mapping, drawing, or solid modeling software to identify physical anomalies. Asymmetry may result if the cornea or sclera are stretched beyond their elastic limits. The single beam unit is expected to be sufficient for IOP measurement, in most instances. Notice that there is no real "zero" since there is always a finite limbus angle. Analytical comparison techniques such as from Fourier or other geometric analysis may be used to extract secondary information from the signatures that may be of value comparable to that of IOP itself, particularly with regard to similarity of response between patients with the same type of glaucoma.

Figure 16:
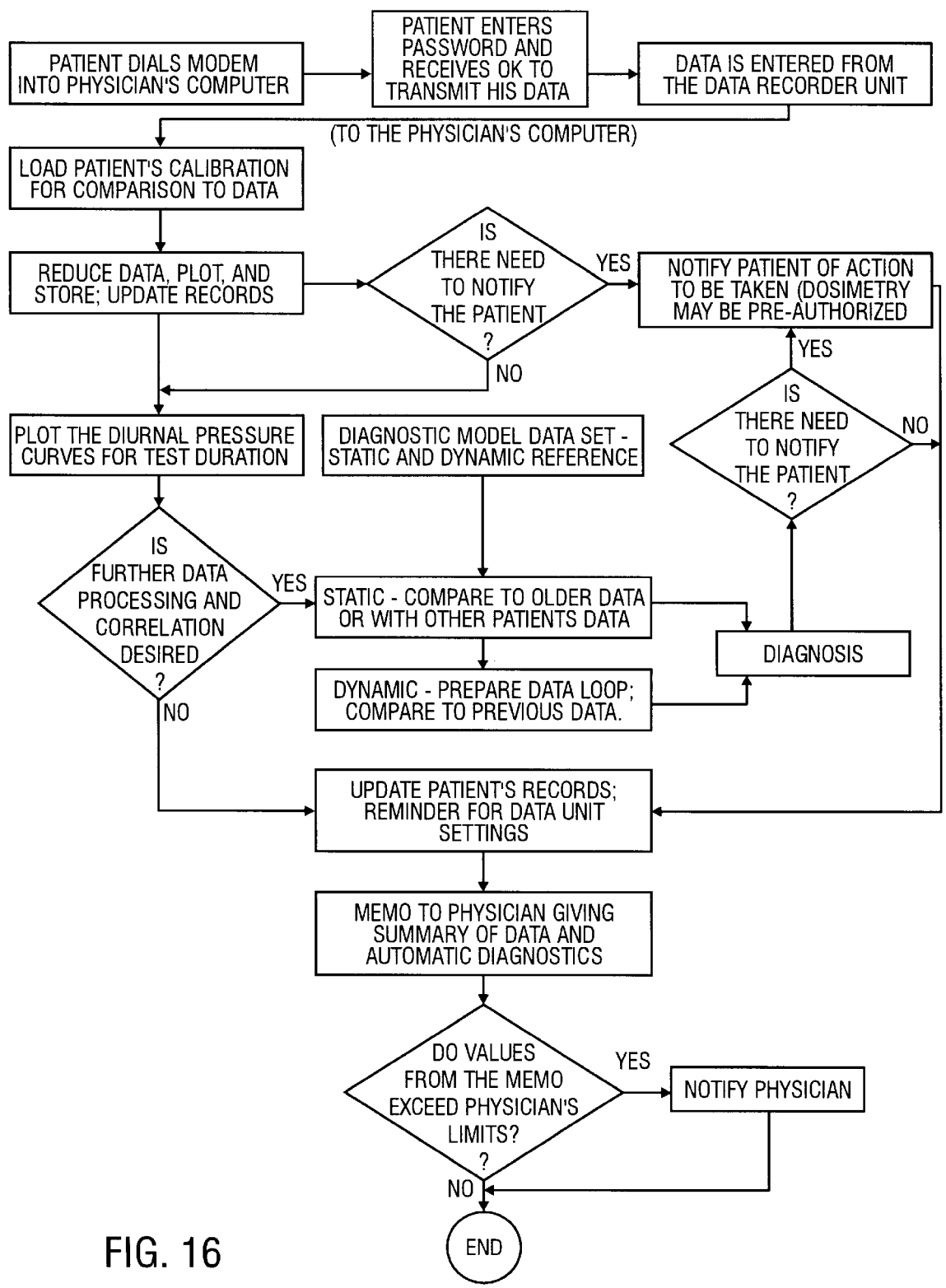
FIG. 16 is a block diagram illustrating a scheme for the processing of data, from either calibration or field acquisition, for diagnosis of intraocular or blood pressure phenomena.

The data unit is as compact as possible, and provides dependable capture of IOP related contour signatures. The data unit contains an EPROM, programmed in accordance with prescription from the physician, to control the storage of data from the ER in RAM. Data is recorded on storage media such as magnetic tape or cards and may be communicated from the patient to the physician's office for analysis. This allows the physician to be involved in the diagnosis and treatment of the patient, to a degree and in a time frame, previously impossible for treatment of glaucoma. The ability to know IOP in nearly real time will be very effective in preventing physiological damage that can cause blindness. FIG. 16 is a flowchart example of data acquisition, reduction, analysis, and handling for the field monitor of IOP or BP.

Since the eyelids are of relatively constant thickness, thereby modifying limbus contour in relatively constant fashion, the possibility of making measurements with eyes closed is feasible, though reflective ointment on the eyelids would be necessary to insure reasonable reflection. This concept is to be evaluated as development of this invention continues. The capability of measuring IOP through the eyelid would be very effective in making automatic measurements of IOP during sleep, when the body's supine position increases the systolic blood pressure component of IOP due to the increase in the heart's height relative to the eye. In many instances the most damaging events to the eye, from glaucoma, occur during sleep.

Example 8

Similar apparatus and procedures may be used to measure blood pressure, blood chemistry, and pulse rate. The pupils of the eyes are the only transparent windows in the body where blood vessels and nerves may be observed without an opaque barrier to their translucent walls. Blood vessels are visible on the surface of the sclera, with a clarity unequaled elsewhere on the body. The opportunity to view these vessels and nerves provides a unique opportunity to use signature analysis techniques to "learn" the nuances of physical shape and color in relationship to health or disorder. The measurement of blood pressure may be deduced from the distortions of blood vessels on the surface of sclera or retina in a manner similar to that described for measuring IOP, i.e., through signature analysis of the reflections from the vessels, in direct comparison to calibration signatures recorded in the physician's office.

Physiological condition related to the color of vessels and nerves are visible in or on the eye. The color of these elements may be quantified by spectrum analysis, where the colors of specific elements may be discretely analyzed to identify and quantify their presence. As an example, the color of the optic nerve is directly related to its health; a healthy nerve being bright orange or pink; fading to a dull gray as it deteriorates or dies.

Blood Pressure and optic Nerve

Similar apparatus to that described for the IOP may be used to measure carotid artery distortions (i.e., changes in the artery's physical size/shape from blood pressure according to the equations of mechanics). The apparatus for making these measurements is not intended for continuous monitor, but to offer enhanced diagnostics of the patient's general health from scans of the eye during routine physician's office visits. Positioning hardware to accurately locate the apparatus for such applications may be used to make complex, yet precise, physiological measurements in both clinical and non-clinical settings.

The images of the carotid arteries are irregular and are not suitable for analysis by the simple beam deflection afforded by the limbus discontinuity for deducing IOP. The mapping of blood vessels and the reflections from them that are indicative of both systolic and diastolic blood pressure components requires that a two dimensional image be constructed to identify specific vessels chosen for data and to record the complex reflections from them. This implies that a rasterized scan of the ER be employed (which then gives, in essence, a video camera). The output from this "camera" may be taken to a "correlator" to analyze the similarity between the calibration recordings taken in the physician's office, and the patient's field data, in the time domain (cross-correlation); the result being a measure of similarity between the signals. Alternatively, the signals from the full ER matrix may be compared, digitally, to determine their similarities. Such similarities are qualitatively related to each other, and may be quantified by comparison to the IOP measured separately on calibration. Further, images from the carotid artery may be compared with images of itself taken at different times (auto-correlation) to quantify change in patient condition. There are numerous other methods of comparing data sets; these are chosen for example, but are not the only means of comparison.

Determination of blood pressure also may be made from similar analysis of the surface blood vessels on the sclera; however, these vessels are smaller, therefore less likely to give the resolution afforded from the carotid. In order to get a good image of the carotid, through the pupil, it is necessary to get close enough to get a full view of the retinal plane. This problem may be alleviated by using a wavelength of light that is not in the visible range, allowing the pupil to remain in relatively dilated condition.

Dynamically varying signals such as those from pulsations of blood vessels due to diastolic variation may be analyzed by Fast Fourier Transform (FFT) methods in a "spectrum analyzer" that processes signals in the frequency domain to quantify harmonic content. In this instance, spectrum refers to the dynamic as opposed to color spectrum. Data from the ER, directly, or from the correlator above, may be edited into "endless loops," or repetitively played from digital storage, for analysis in the frequency domain. Since correlation functions of periodic functions also are periodic, at the same frequency, correlation functions may be FFT processed in the frequency domain (cross power spectral density) to sharpen the desired dynamic components such as from diastolic blood pressure variation. The diastolic components also may be isolated by digital comparison of images from successive raster scans from the ER, with the extreme variations defining the sum and difference of systolic and diastolic components, respectively, all of which are related to the calibration images taken at known pressures.

The color spectrum of reflections from the nearly transparent walled carotid artery may provide discretely identifiable signatures related to blood sugar, oxygen, alcohol levels, etc., to allow virtually instantaneous blood chemistry analysis. The spectrum of the optic nerve is qualitatively related to its health, with a healthy nerve being a bright red-orange or pink, fading to a dull gray as the nerve deteriorates or dies. Color spectrum signature analysis according to modern methods such as from imaging spectrographs (Purcell, 1993) provides powerful diagnostics for general patient monitoring. Comparisons between spectra of patients with the similar disorders may provide direct diagnosis of numerous disorders.

In summary, the eye is the only transparent window in the body where direct observation of critical blood vessels and nerves, that respond to numerous disorders, is afforded. Response to these disorders may be characterized by observing signatures from the vessels or nerves themselves and comparing them to related physiological functions that are measured, independently, by conventional methods at the same time. Correlations between these phenomena allow recording of images in non-clinical settings from which deductions of the related functions are obtained in short time frame.

Example 9

The reduction of data for IOP is relatively simple and consists of comparing data defining the limbus contour against the calibration standards for that eye where data are taken under controlled clinical conditions with separately measured pressure and angles of elevation. Data processing includes determination of the deflection and angle relative to the ER and interpolation to give IOP.

Blood pressure, or BP, processing is more difficult and requires that the image of the vessel, chosen to determine the pressure related signatures, be corrected for position and orientation before the comparison is made. This implies that a reference point, and angular reference must be used to bring both calibration and data sets into physical register with each other. Magnification may be reasonably stabilized by precision placement of the scanning unit (as may the angular orientation) which is connected to the patient's data unit in either case. A separate unit seems superior to any continuously worn, or "integral" apparatus, since special provisions for precision placement, and exclusion of ambient interference would be better afforded.

Data Processing

As mentioned in the introduction above, determination of IOP is a relatively simple process involving the comparison of the peak deflection of a data beam, as recorded in the patient's data unit to the beam deflections that occurred with the same apparatus during calibration in the physician's office. This requires little beyond applying linear interpolation between, or extrapolation beyond, the calibration curve IOP increments, induced in the physician's office, to the measured peak beam deflections observed in the data. The angular path over the ER during beam deflection gives the elevation of the eye. The IOP is determined by double interpolation between angle and peak beam deflection to give the IOP. Since the devices for an ER are of the digital matrix type, or an analog type that may be converted to digital format, pixels defining rows and columns, sensitive to light give the instantaneous position of the reflected beam. If data is recorded for a window in time, the excursion of the beam over the ER is faithfully recorded. The "jump" at the discontinuity gives both limbus angle and azimuth related to the angle of elevation. Such data may be processed and compared with the calibration references in a fraction of a second for virtually real time indication of IOP.

Data reduction for BP measurement is more complicated. The image of the carotid artery is complex, with little or no correlation between patients; nor is there any symmetry or discrete geometric discontinuity as with the external surface of the eye at the limbus. The task is to relate the two-dimensional images, of the carotid or scleral vessels on the ER, to BP. This requires that separate images of the carotid from the ER be compared, with the difference between them being the signature to be related to pressure. In this instance, it is first necessary to correct for positional differences of images on the ER. Some major feature is chosen as "Zero" reference and the images are "corrected" to the same reference.

It is expected that position and magnification may be sufficiently maintained to preserve scale reference for the image. The reference should be as discrete a point as may be identified, for the specific patient, and the alignment or rotational orientation of the image be positively identified either by physical registry of the apparatus or by a second image comparison. There are numerous geometric analysis programs that may be used to process the data from the pixels to identify these features. This allows correction of the images to a common origin, angular orientation, and scale. Differences between subsequent image matrices, for determination of systolic pressure and diastolic variation, compared with the references taken for calibration, give the signatures that may be used to measure BP. Several comparisons must be made to establish both systolic and diastolic components of blood pressure to insure that both high and low peaks of distortion from diastolic pressure are obtained. The determination of BP requires some process time, but may be quicker than that for conventional sphygmomanometer and at a fraction of the size and weight. In this instance, the data unit will be larger than that for IOP due to the greater requirement for full, multiple, image processing and differencing. Current "palm-top" computers have adequate storage and processing capability. The "separate" package for the sensors and ER array may be of the size of a pack of cigarettes or so. These package sizes may be expected to shrink with the trend in instrument development to smaller packages. Alternatively, the unit may be configured to store the corrected images in a simple, and physically smaller, memory for subsequent transmission to the physician's office for processing. Sequential images at high storage rates may be used to reconstruct the dynamic character of BP including "murmurs" or other anomalies.

Complex color spectral data may be recorded (Purcell, 1993). These data are not expected to be highly dynamic; however, data will be evaluated at sufficient data rates to determine if high rate changes in color spectra occur during strenuous or stressful situations. The use of spectrographic imaging may be used to isolate specific dynamic temperature variations from color photothermography (colors proportional to temperature). While there might be some value in ambulatory monitor of color spectra, this is expected to be primarily a clinical unit used for checks during routine office visits, etc. A special CCD color spectral processor could be made pocket size; again, with a separate recording media for storing the images.

Reference

Purcell, Frank in Laser Focus World, "Imaging Spectrographs Performed Multidimensional Spectroscopy," May 1993, pp. 93–97

What is claimed is:

1. An intraocular pressure measuring apparatus comprising:
   a light emitter means for emitting a light beam spaced or swept across the outer surface of a limbus region between the sclera and cornea of the eye;
   at least one photo detector spaced relative to the emitter wherein said photodetector converts to electrical signals the position of a light beam reflected from the limbus region;
   an analog-to-digital converter coupled to the photo detector that encodes the electrical signals to digital data; and
   a local memory medium means connected to the converter for accumulating the digital data over a period of time wherein changes in contour of the limbus region that are caused by alterations in intraocular pressure without contact or force applied to the eye measurably affect the electrical signals generated in response to the position of the reflected light beam.

2. The apparatus as recited in claim 1, further comprising an eyeglass frame or light opaque enclosure wherein said apparatus is mounted in fixed register to the eye and adjustable positioned in close proximity to the limbus region, the light emitter or multiple emitters and photo detector being coupled to a localized portion of said eyeglass frame or opaque enclosure.

3. The apparatus as recited in claim 2, wherein the light emitter and photo detector are fixed in spaced relation to each other and wherein the beam from the emitter angularly sweeps repetitively across the limbus region.

4. The apparatus as recited in claim 1, wherein the light emitter comprises a light emitting diode.

5. The apparatus as recited in claim 1, wherein the light emitter comprises a laser.

6. The apparatus as recited in claim 1, wherein the local memory medium comprises a read/write device carried with a patient undergoing intraocular pressure measurement or blood pressure measurement.

7. The apparatus as recited in claim 1 further comprising a remote memory medium means for receiving downloaded digital data from the local memory medium; and
   a signal processor coupled to the remote memory medium wherein intraocular pressure and blood pressure are determined as a function of the digital data.

8. The apparatus as recited in claim 1, wherein the light emitter and detector are coupled to a scanner which moves the emitter and detector in close proximity across the outer vessel surface.

9. The apparatus as recited in claim 8, wherein the scanner comprises:
   a platform having the emitter and detector fixed in spaced relation to one another; and
   a motor drive source attached to the platform for scanning the platform across the outer vessel surface.

10. The apparatus as recited in claim 1, further comprising a local memory medium for storing the electrical signal comprising:
   A first remote memory medium means for accumulating a set of stored values to allow conversion of alterations in the electrical signal to changes in intraocular pressure;
   A second remote memory medium means for accumulating a set of stored values to allow conversion of alterations in the electrical signal to changes in blood pressure; and,
   A computer means for converting connected to the first and second memory media alterations in the electrical signal to intraocular pressure and blood pressure.

11. A method for measuring changes in intraocular pressure within an eye, comprising:
   repeatedly scanning a light beam across a limbus region between the sclera and cornea of an eye without concurrent application of force or contact with the eye, producing a light beam reflected from the limbus region;

repeatedly detecting alterations of the light beam reflected from the limbus region; and converting alterations of the light beam to changes in intraocular pressure.

12. The method as recited in claim 11, wherein repeatedly scanning comprises linearly moving the light beam across the limbus region.

13. The method as recited in claim 11, wherein repeatedly scanning comprises substantially continuously scanning the light beam across the limbus region.

14. The method as recited in claim 11, wherein alterations of the light beam reflected from the limbus region are measured as changes in intensity.

15. The method as recited in claim 11, wherein alterations of the light beam reflected from the limbus region are measured as changes in position.

* * * * *